United States Patent
Scarfogliero et al.

(10) Patent No.: US 9,028,468 B2
(45) Date of Patent: May 12, 2015

(54) ROBOTIC APPARATUS FOR MINIMALLY INVASIVE SURGERY

(75) Inventors: Umberto Scarfogliero, Lucca (IT); Claudio Quaglia, Pontedera (IT); Marco Piccigallo, Pisa (IT); Selene Tognarelli, Montignoso (IT); Pietro Valdastri, Leghorn (IT); Arianna Menciassi, Pontedera (IT); Paolo Dario, Leghorn (IT)

(73) Assignee: Scuola Superiore di Studi Universitari e di Perfezionamento Sant'anna, Pisa (IT)

( * ) Notice: Subject to any disclaimer, the term of this patent is extended or adjusted under 35 U.S.C. 154(b) by 0 days.

(21) Appl. No.: 13/642,509

(22) PCT Filed: Apr. 22, 2011

(86) PCT No.: PCT/IB2011/051772
§ 371 (c)(1),
(2), (4) Date: Jan. 23, 2013

(87) PCT Pub. No.: WO2011/135503
PCT Pub. Date: Nov. 3, 2011

(65) Prior Publication Data
US 2013/0131695 A1   May 23, 2013

(30) Foreign Application Priority Data

Apr. 26, 2010  (IT) ................. FI2010A0075

(51) Int. Cl.
*A61B 19/00*   (2006.01)
(52) U.S. Cl.
CPC ..... *A61B 19/2203* (2013.01); *A61B 2019/2234* (2013.01)
(58) Field of Classification Search
CPC .......... A61B 17/00; A61B 5/05; A61B 17/04; G06F 19/00; B25J 15/02
USPC ............. 74/490.01, 6, 443; 227/178.1; 318/568.21; 600/417; 700/245; 475/226; 606/1, 130
See application file for complete search history.

(56) References Cited

U.S. PATENT DOCUMENTS 3,469,470 A * 9/1969 Gaudry ..................... 74/443
4,938,099 A * 7/1990 Knight ...................... 475/226
(Continued)

FOREIGN PATENT DOCUMENTS

| EP | 1 815 950 A1 | 8/2007 |
| EP | 1 886 633 A2 | 2/2008 |

(Continued)

OTHER PUBLICATIONS

Song, H. et al. "The Development of human-arm like manipulator for Laparoscopic Surgery with Force sensing", Industrial Technology, 2006. ICIT 2006. IEEE International Conference. Dec. 2006, pp. 1258-1262.*

(Continued)

*Primary Examiner* — William Thomson
*Assistant Examiner* — Victor Shapiro
(74) *Attorney, Agent, or Firm* — Steinfl & Bruno LLP

(57) ABSTRACT

A robotic arm especially suited for laparoscopic surgery, having a torsional joint and a flexural joint forming serially arranged joints is described. The joints provide respective degrees of freedom for the arm, which further receives drive means for such joints. The robotic arm also has transmission means placed between the drive means have and the joints. The transmission means a first and a second assembly of three gear wheels, preferably conical gear wheels, and a train of three additional gear wheels, preferably straight-cut gear wheels, which couple the first and second assembly to form a differential mechanism.

10 Claims, 23 Drawing Sheets

(56) References Cited

U.S. PATENT DOCUMENTS

| | | | |
|---|---|---|---|
| 5,355,743 A * | 10/1994 | Tesar | 74/490.03 |
| 5,397,323 A * | 3/1995 | Taylor et al. | 606/130 |
| 6,394,998 B1 * | 5/2002 | Wallace et al. | 606/1 |
| 6,516,681 B1 * | 2/2003 | Pierrot et al. | 74/490.01 |
| 7,248,944 B2 * | 7/2007 | Green | 700/245 |
| 7,963,433 B2 * | 6/2011 | Whitman et al. | 227/178.1 |
| 8,109,173 B2 * | 2/2012 | Kinoshita et al. | 74/490.06 |
| 8,374,677 B2 * | 2/2013 | Piferi et al. | 600/417 |
| 8,516,917 B2 * | 8/2013 | Zhao | 74/490.01 |
| 8,541,970 B2 * | 9/2013 | Nowlin et al. | 318/568.21 |
| 2003/0221504 A1 | 12/2003 | Stoianovici et al. | |
| 2004/0049205 A1 | 3/2004 | Lee et al. | |
| 2004/0260334 A1 | 12/2004 | Braun | |
| 2007/0089557 A1 | 4/2007 | Solomon et al. | |
| 2008/0110958 A1 | 5/2008 | McKenna et al. | |
| 2010/0011900 A1 | 1/2010 | Burbank | |

FOREIGN PATENT DOCUMENTS

| | | |
|---|---|---|
| EP | 1 977 713 A2 | 10/2008 |
| WO | 2007/146987 | 12/2007 |

OTHER PUBLICATIONS

Instruction Manual HTM.25 Gear Trains Apparatus, HTM.25. Issue I. Jan. 1994, pp. 2 and 3.*

Song, H. et al. "The Development of human-arm like manipulator for Laparoscopic Surgery with Force sensing", *Industrial Technology*, 2006. ICIT 2006. IEEE International Conference. Dec. 2006, pp. 1258-1262.

Palep, H. "Robotic assisted minimally invasive surgery". Journal of Minimal Access Surgery. 5(1). 2009.

Oleynikov, D. et al. "Miniature robots can assist in laparoscopic cholecystectomy." Surg Endosc., 2005, 19:473-476.

PCT International Search Report for PCT/IB2011/051772 filed on Apr. 22, 2011 in the name of Scuola Superiore Di Studi Universitari E Di Perfezionamento Sant'Anna. Mail Date: Aug. 19, 2011.

PCT Written Opinion for PCT/IB2011/051772 filed on Apr. 22, 2011 in the name of Scuola Superiore Di Studi Universitari E Di Perfezionamento Sant'Anna. Mail Date: Aug. 19, 2011.

* cited by examiner

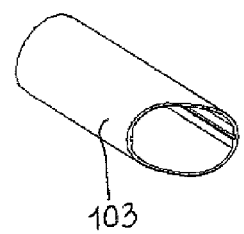
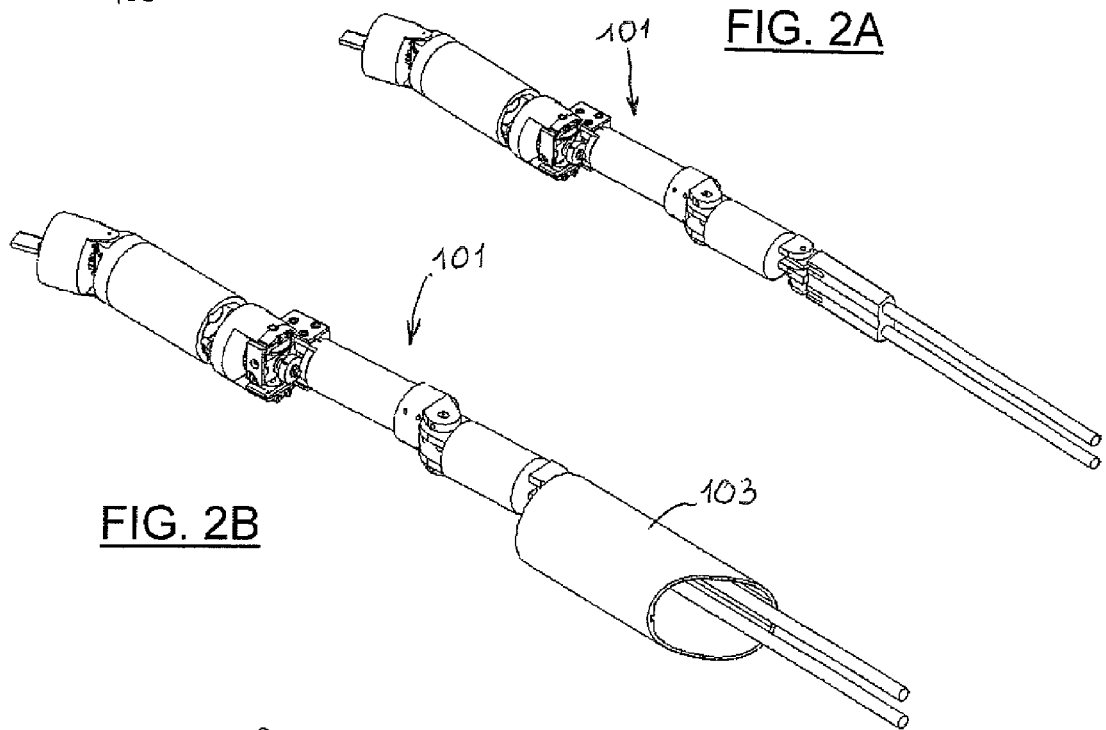
FIG. 2A
FIG. 2B
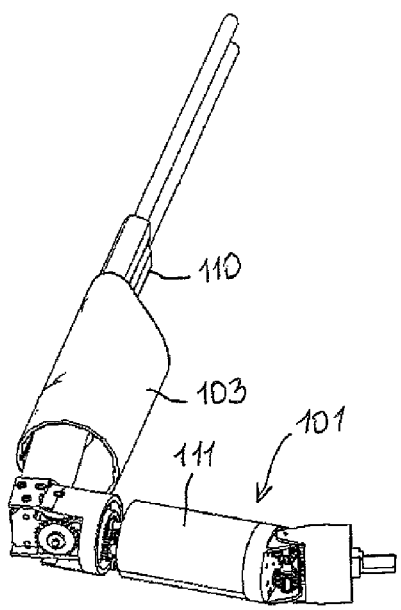
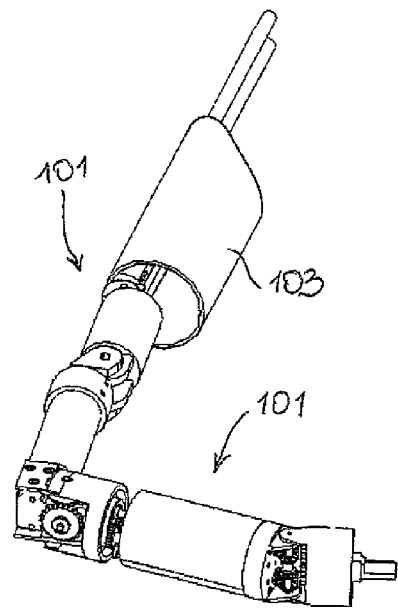
FIG. 2C
FIG. 2D

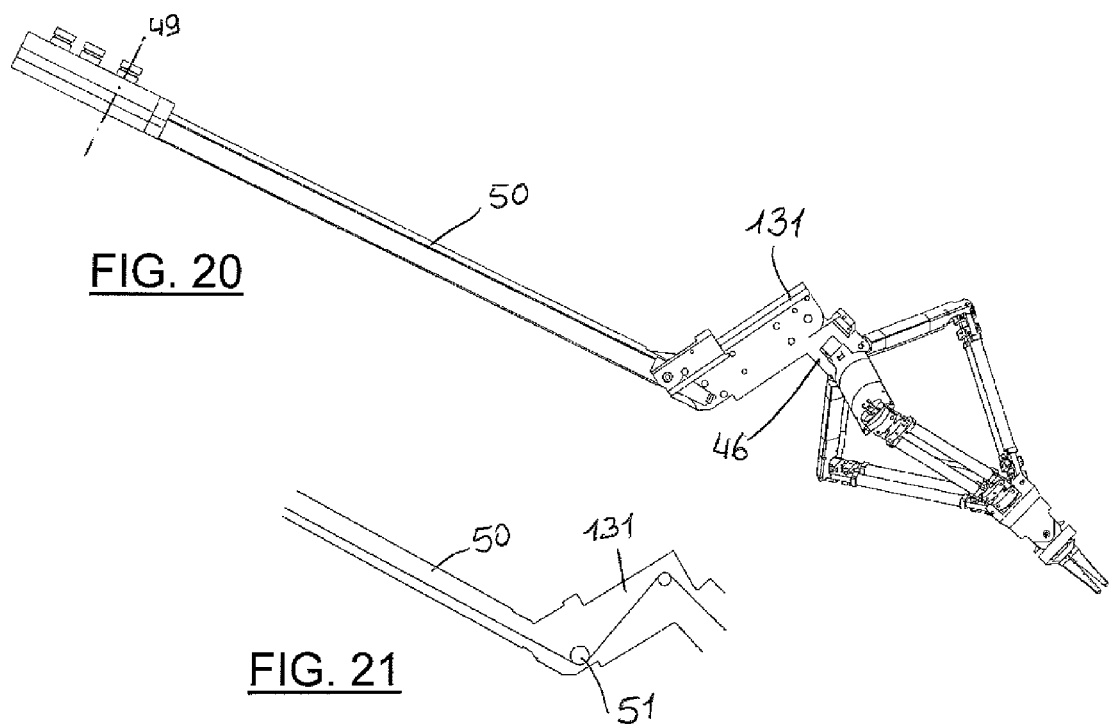
FIG. 20
FIG. 21
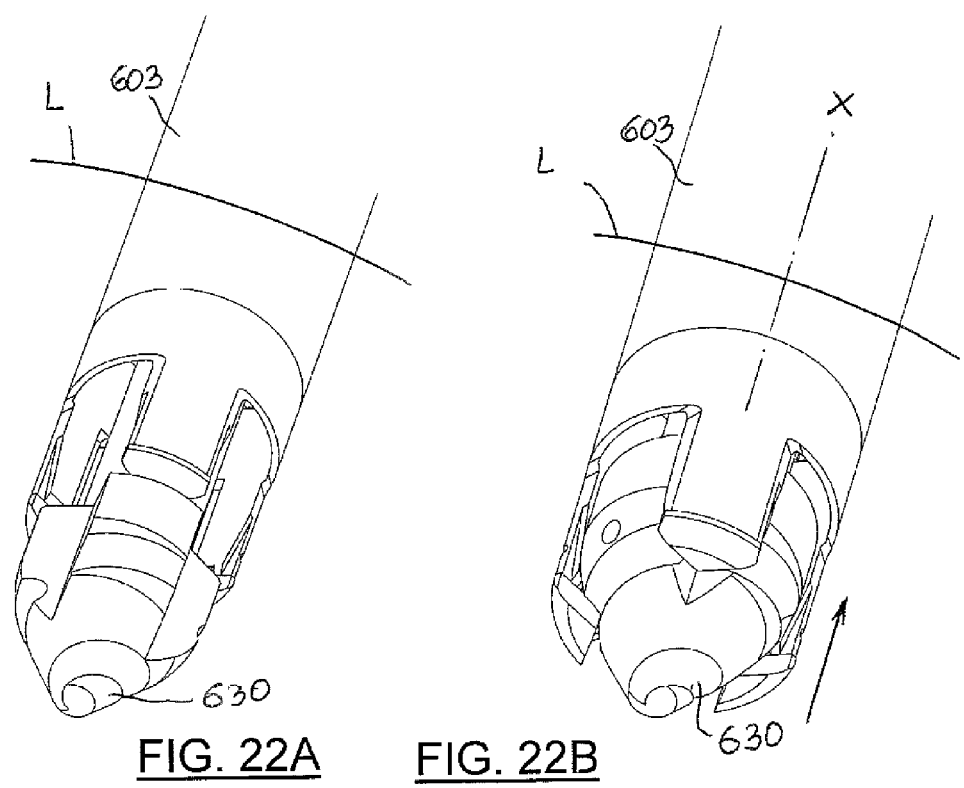
FIG. 22A          FIG. 22B

US 9,028,468 B2

ROBOTIC APPARATUS FOR MINIMALLY INVASIVE SURGERY

CROSS REFERENCE TO RELATED APPLICATIONS

The present application is the US national stage of International Application PCT/IB2011/051772filed on Apr. 22, 2011, which, in turn, claims priority to Italian Patent Application FI2010A000075filed on Apr. 26, 2010.

FIELD OF THE INVENTION

The present invention refers to a robotic apparatus for minimally invasive surgery (hereinafter referred to as mini-invasive for the sake of simplicity), in particular laparoscopic surgery.

STATE OF THE ART

In the conventional surgery procedures, or open surgery, the surgeon generally performs a very long incision. After this, the surgeon intervenes on the part of interest manually or using manually actuated instruments. Thus, the surgeon has the following advantages:
  stereoscopic vision—and thus the perception of the relative distances—due to the direct vision between the surgeon eyes and the operation scenario;
  feedback force and natural sense of touch, given that the surgeon uses his hands to exert forces on the tissue in a direct manner or at least mediated by a single instrument.

The most relevant negative aspect of conventional surgery is related to the high invasiveness of the procedure, hence implying long recovery periods.

In the abdominal surgery, a considerable improvement in terms of lower invasiveness was obtained through the introduction of laparoscopic techniques. In this case, between three and five small incisions (typically between 3 mm or 5 mm, at times 8 mm long) are performed in the body of the patient and, the surgery is performed after insufflating the abdominal cavity. Typically, an incision is used for the passage of a camera while operation or assistance instruments are introduced from the other two. The laparoscopy operation instruments are passed through a support tubular body transcutaneously inserted into the incision and called trochar, which provides a so-called abdominal "port".

From a surgical point of view, the laparoscopic procedure is much more complex as compared to the conventional surgery due to the following reasons:
  the field of vision and the quality of the vision are low, given that a two-dimensional camera is generally used and thus stereoscopy as well as the relative perception of the distance, typical of conventional surgery, is lost;
  the movement of the surgical instrument is inverted with respect to the hand of the surgeon, due to the fulcrum effect typical of the laparoscopy instruments;
  the feedback force is distorted by the presence of the trochar;
  the dexterity of the instruments is considerably limited to a few degrees of freedom.

On the other hand, the invasiveness of the laparoscopic procedures allows considerably reducing the hospitalisation time.

Some of the aforementioned disadvantages of laparoscopy are overcome by the so-called "Da Vinci" system (H. Palep: *Robotic assisted minimally invasive surgery,*in *Journal of Minimal Access Surgery*, vol. 5, issue 1, 2009), the only example of robotic laparoscopy surgery platform available in the market. Such platform is constituted by two main parts, and precisely a "master" control console, where the surgeon has the possibility of seeing the operation scenario on a three-dimensional display and remote-operation of four robotic arms, and a "slave" robotic system, constituted by the aforementioned robotic arms (three having an 8 mm diameter for laparoscopic instruments and one having a 12 mm diameter for the stereoscopic vision system). An additional hole for the passage of the surgical operation support instruments (for example sponges, needle and suture thread, haemostatic forceps, etc.) should be added to the four holes for the aforementioned instruments.

The main advantages introduced by the Da Vinci system with respect to the conventional laparoscopic procedures consist in:
  stereoscopic vision, thus a better perception of the distances;
  intuitive control, in that the robotic approach allows compensating the fulcrum effect typical of the laparoscopic instruments;
  scaling the work space, due to which an extensive movement of the surgeon's arm on the master corresponds to a slight but highly accurate movement of the robotized instrument;
  dexterity comparable to the hand of the surgeon, due to the seven degrees of freedom typical of each operating arm of the Da Vinci system.

It is also true that the Da Vinci system revealed various drawbacks which allow use thereof only for highly selected and particular procedures. Such drawbacks include:
  high cost;
  long periods of preparation;
  overall dimension of the external robotic arms;
  increase of invasiveness with respect to laparoscopic surgery procedures (a total of five holes, with a 12 mm hole, three 8 mm holes and a 5 mm hole);
  lack of feedback force (which cannot be obtained from the information of the current in the motors in that, due to the external cable actuation, it cannot be considered proportional to the force exerted by the end effector).

A very promising alternative approach seems to be that of the so-called *Robotic NOTES* (*Natural Orifice Transluminal Surgery*). Such approach is currently applied only at research level (D. Oleynikov, M. Rentschler, A. Hadzialic, J. Dumpert, S. R. Platt, S. Farrito: *Miniature robots can assist in laparoscopic cholecystectomy, Surg Endosc.*, vol. 19, pages 473-476, DOI: 10.1007/s00464-004-8918-6, 2005). In this case, a "self-powered" mini-robot is introduced into the body of the patient through a natural orifice (or a single abdominal port) and locked therein through magnetic systems or using needles. Invasiveness is reduced to the minimum in this case, due to the fact that transcutaneous holes into the body of the patient cannot be avoided, eliminating risks of infection and scars.

The main drawbacks of this approach are:
  dexterity, still very limited as for now;
  low power, due to the fact that all the actuators are provided on board the robot.

Regarding the latter aspect, given that the robot should pass through natural lumen or through a single access port, the dimensions thereof should necessarily be minimum thus implying the use of motors of smaller dimensions and consequently having low power. Therefore, the NOTES approach is not capable of guaranteeing the performance of the Da Vinci system in terms of motion speed of the instrument and tractive force. The latter aspect is also related to the lack of a stable rigid support for the operating arms capable of allowing exerting considerable amounts of force into the manipulation for surgery tasks.

Thus, in summary the current solutions for laparoscopic surgery based on robotic arms maneuvered from outside provide for cumbersome units and thus require more invasive incisions with respect to the conventional laparoscopic surgery techniques (already deeply consolidated in modern surgery). On the other hand, the other solution based on robots navigating in the body is still at the embryonic stage and it seems not capable of guaranteeing the stability, dexterity and power required for surgery in the abdominal cavity.

Therefore, the known systems do not achieve an optimal compromise among dexterity, power and degrees of freedom on one hand and mini-invasiveness (also with the possibility of a single access port) on the other. In particular, as previously mentioned, the systems that allow operating in minimum invasiveness conditions with a single access port or through a natural orifice do not allow achieving the stability and power required for abdominal surgery.

In particular, one of the problems associated to the above-mentioned drawbacks is that of obtaining a satisfactory rigidity of the kinematic chain of the robotic arms actuable from outside and a reduction of the relative mechanical clearances, and at the same time providing an effective on board actuation of the distal joints of the robotic arm.

SUMMARY OF THE INVENTION

Thus, the technical drawback addressed and resolved by the present invention is to provide a robotic apparatus for laparoscopic operations capable of allowing overcoming the previously mentioned drawbacks with reference to the prior art.

Such problem is resolved by a robotic apparatus according to claim 1.

Preferred characteristics of the present invention are set forth in the dependent claims thereof.

The present invention provides some relevant advantages. The main advantage lies in the fact that it provides a differential mechanism which is particularly efficient and small in size, suited for the transmission of motion in any miniaturized system which receives or is adapted to receive means for driving a flexural joint and a torsional joint serially arranged, given that it can be interposed between such drive means and said joints.

Other advantages, characteristics and methods of use of the present invention shall be apparent from the following detailed description of some embodiments, provided by way of non-limiting example.

BRIEF DESCRIPTION OF THE DRAWINGS

Reference shall be made to the figures of the attached drawings, wherein:

FIGS. 2A to 2I each show a perspective view of the apparatus of FIG. 1 in a step for inserting a relative arm through an introducer body which serves as laparoscopic access port;

FIGS. 20 and 21 refer to a mechanism for actuating proximal joints of the robotic arm of FIG. 19A, 19B, respectively showing a perspective view of the mechanism and a lateral view of a detail of the latter thereof;

FIGS. 22A, 22B and 22C each show a perspective view relative to a variant of an introduction system;

DETAILED DESCRIPTION OF THE INVENTION

General Structure of the Robotic Apparatus

Figure 1:
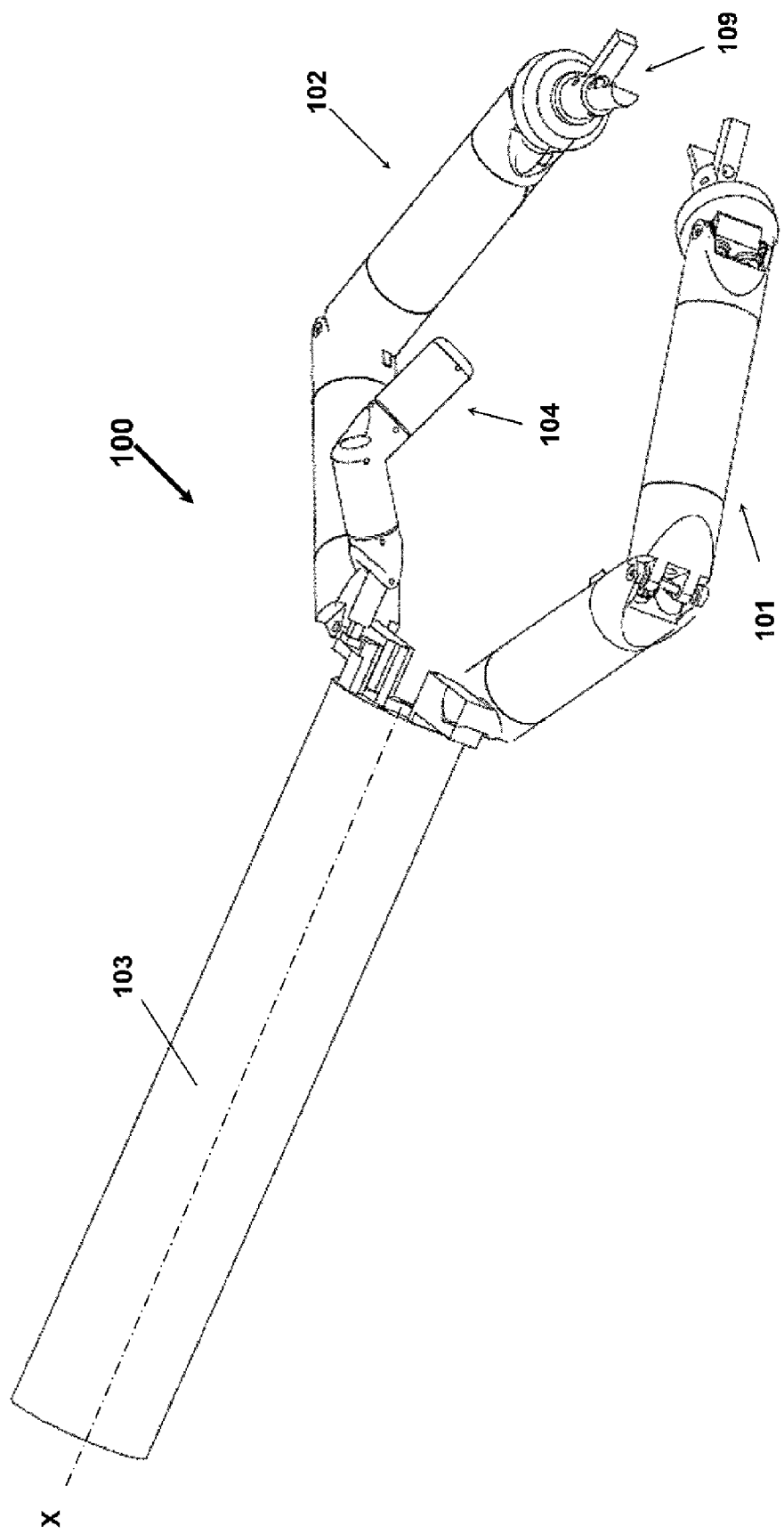
FIG. 1 shows a perspective schematic view of a preferred embodiment of a robotic apparatus according to the invention, in an exemplifying configuration with two arms (bi-manual), each of which has a serial structure, i.e. with a serial arrangement of relative rotary joints.

With initial reference to FIG. 1, a robotic apparatus for laparoscopic surgery according to a preferred embodiment of the invention is indicated in its entirety with 100.

In such figure, the apparatus 100 is represented in an exemplifying configuration which provides for a first and a second robotic arm, respectively indicated with 101 and 102, each having a plurality of articulated joints arranged longitudinally along the arm according to a serial structure. In particular, each arm 101, 102 has six degrees of freedom. The distal end portion (with respect to the surgeon) of each robotic arm 101, 102 may be equipped with surgical instruments, such as for example forceps 109, or with sensors, such as cameras or biometric sensors.

Alternative configurations of the apparatus 100 will be described hereinafter with reference for example to FIG. 27, in which the apparatus comprises a serial arm 101 and two hybrid parallel/serial structure arms respectively indicated with 201 and 202.

Thus returning to FIG. 1, the apparatus 100 also comprises a support body 103, or introducer, having a cylindrical-shaped tubular structure in its entirety analogous to and compatible with that of a trochar. The support body 103 has a symmetrical longitudinal axis indicated with X in FIG. 1.

The support body 103 is thus adapted to serve as an introducer for the arms 101 and 102 into the body of the patient, allowing the passage of both through it.

The apparatus 100 further comprises a stereoscopic vision system 104, schematically represented in FIG. 1. Such vision system 104 may be associated to one of the arms 101 or 102 or introduced through the support body 103 with other means.

Exemplifying Method for Inserting the Serial Robotic Arms Through the Introducer Body As mentioned above, the introducer body 103 is conceived to allow the introduction of the robotic arms of the apparatus 100 into the body of the patient.

A preferred introduction method provides for the insertion of one robotic arm at a time. FIGS. 2A to 2I thus show, schematically and in sequence, how each of the robotic arms 101 and 102 is inserted, during a laparoscopic surgery, through the introducer body 103.

In particular, as shown in FIGS. 2A and 2B, during the insertion the first arm 101 is arranged longitudinally in the introducer body 103 in a rectilinear alignment configuration of the joints thereof.

Figure 3:
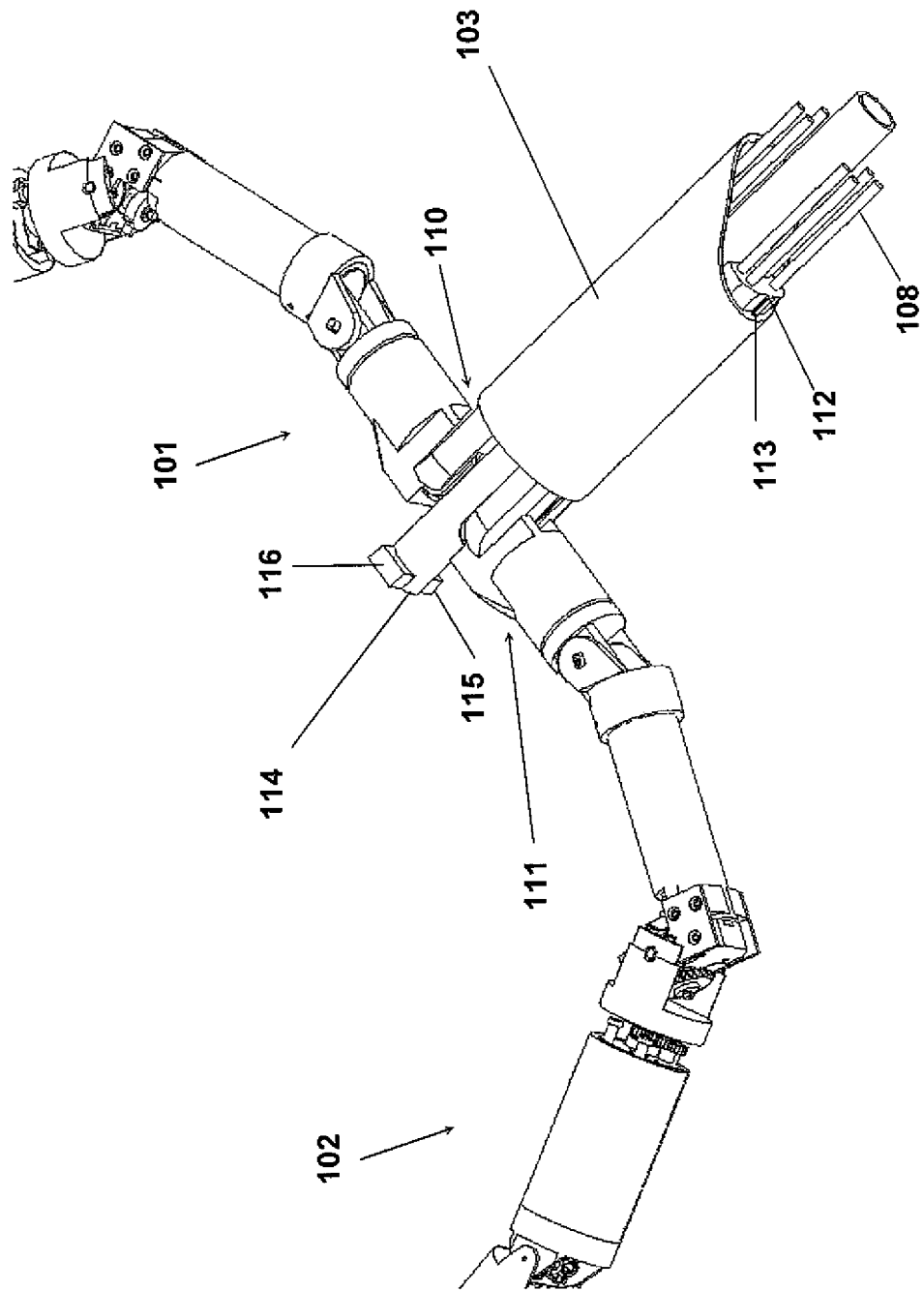
FIG. 3 shows a perspective rear view of part of the robotic apparatus of FIG. 1 showing relative means for locking the arms on the introducer body according to a first variation.
Figure 4A:
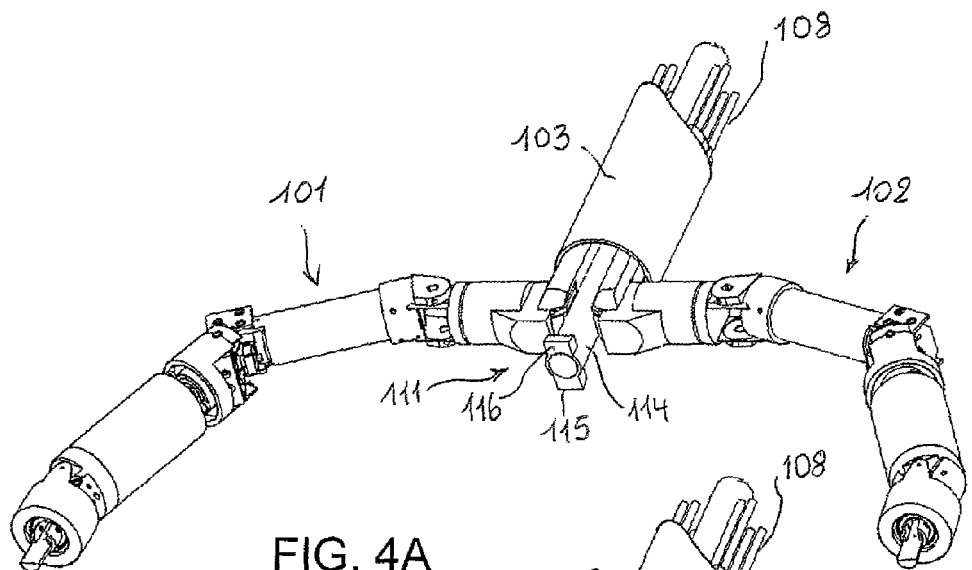
FIGS. 4A, 4B and 4C each show a perspective front view of the robotic apparatus of FIG. 3 in a respective step of the procedure for locking the relative arms on the introducer body.
Figure 4B:
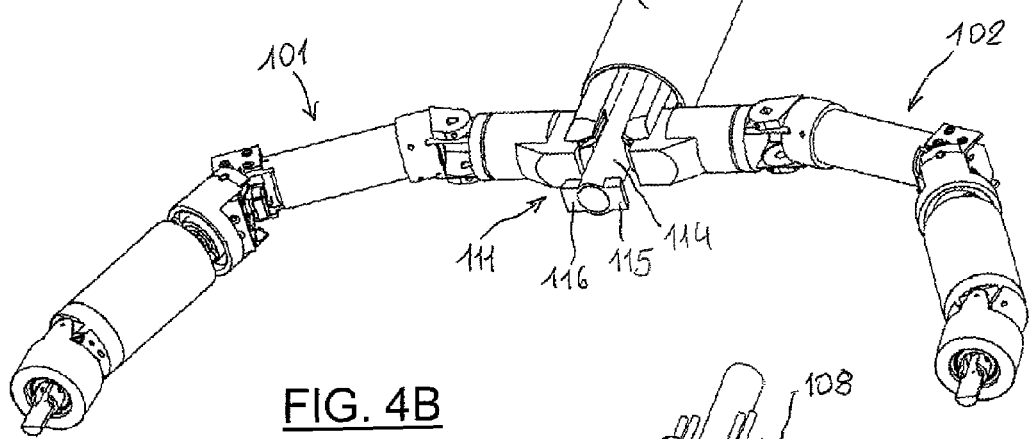
Figure 4C:
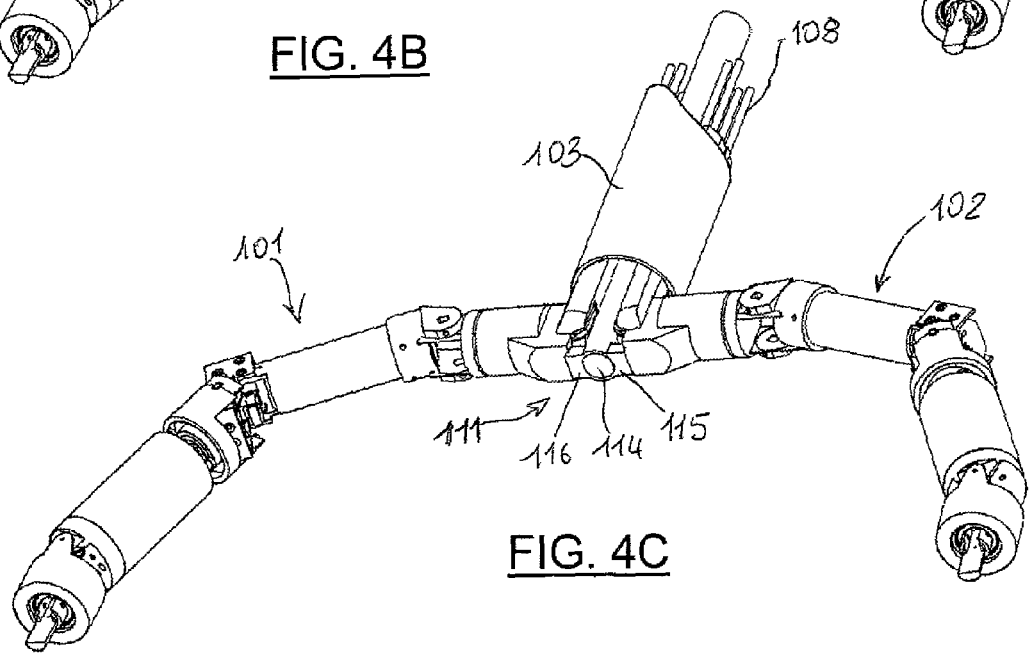

During such insertion, the arm 101 and body 103 are slidably coupled through respective complementary engaging means, better observable in FIG. 3. In the present example, such engaging means comprise a longitudinal face 112 projecting from a first basic proximal portion 110 of the arm 101 and adapted to slide in a respective groove 113 provided in the inner wall of the support body 103.

Now, with reference to FIGS. 2C, 2D, 2E and 2F, once a second proximal portion 111 of the arm 101 exits from the introducer body 103 within the abdominal cavity or any other body region, the proximal joints of the arm 101 are actuated (according to the methods to be described hereinafter) so as to allow a substantially 90 degrees rotation of the most proximal joint outwards relative to the longitudinal axis of the introducer body 103.

Figure 2E:
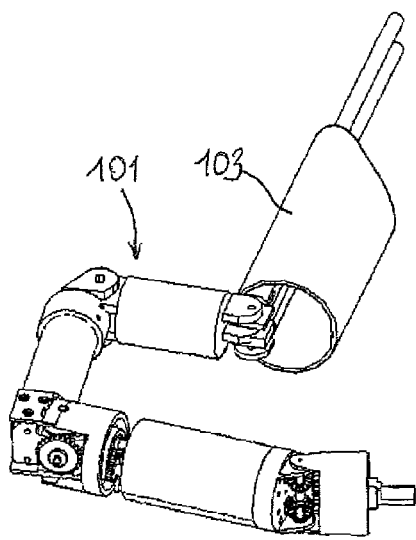
Figure 2F:
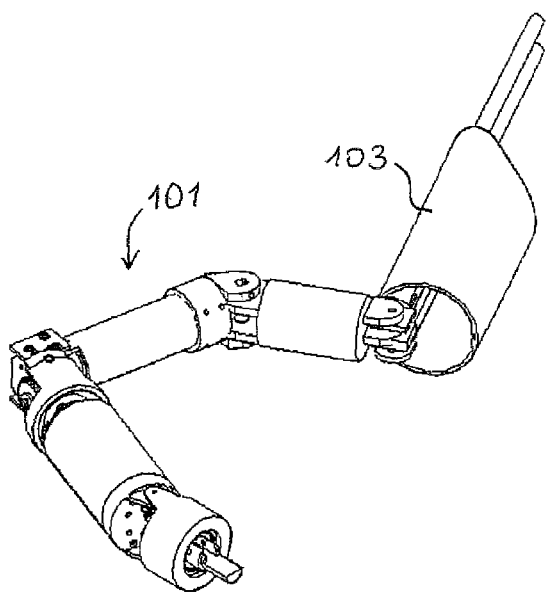
Figure 2G:
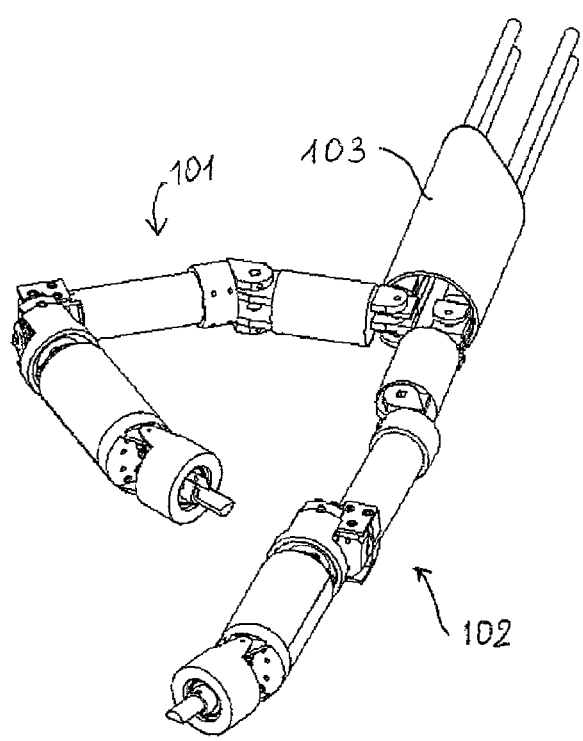
Figure 2H:
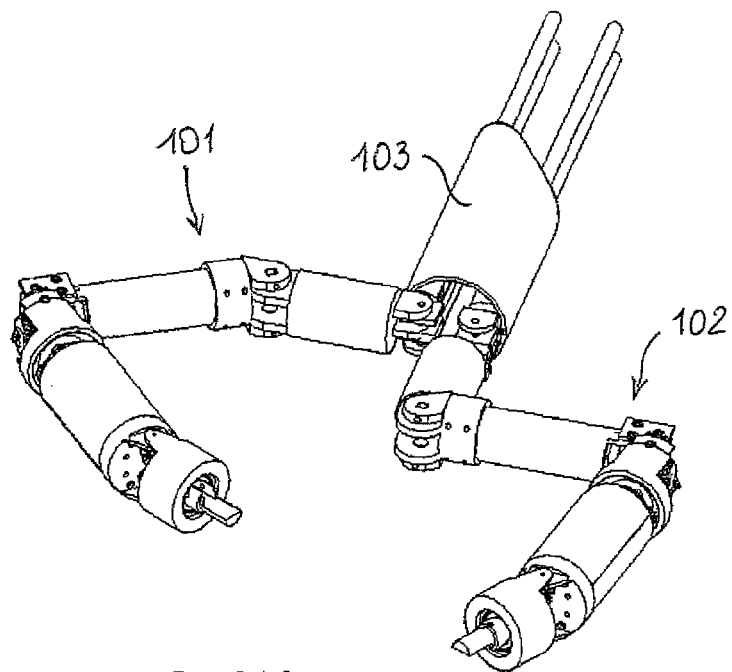
Figure 2I:
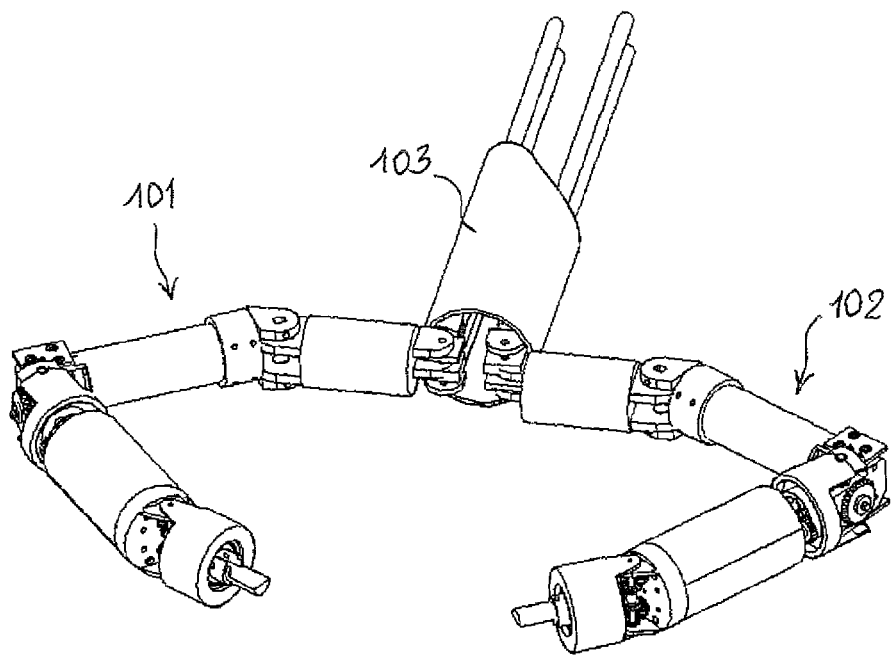

With reference to FIGS. 2G, 2H and 2I, the second arm 102 is thus introduced, according to methods similar to those described above regarding the first arm.

Once taken to the introduced configuration of FIG. 2I, the arms 101 and 102 are locked on the introducer body 103 according to the methods to be described below.

First Method for Locking the Robotic Arms on the Introducer Body

With reference to FIG. 3, as mentioned above each robotic arm 101, 102 has a first basic proximal portion 110 adapted to be slidably coupled with the inner wall of the introducer body 103.

Furthermore, still as previously mentioned, each robotic arm 101, 102 has a second proximal portion 111, arranged distally with respect to the first proximal portion and associated to the abovementioned plurality of articulated joints and in turn articulated to the basic portion 110 so as to be able to rotate by about 90 degrees with respect to the latter, i.e. with respect to the longitudinal axis X of the introducer body 103. Such "folding" of the arm may be either passive or externally actuated, for example through cable actuation systems or other mechanical transmission means of per se known type.

Figure 5A:
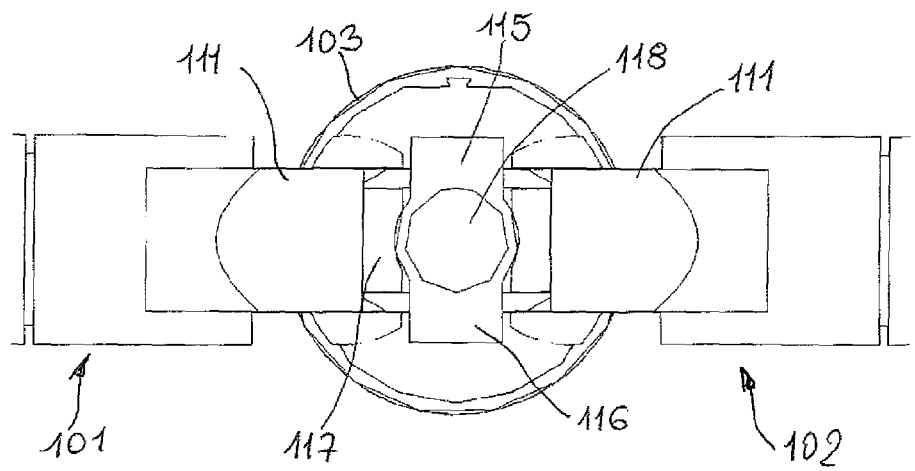
FIGS. 5A and 5B each show a respective front view of the robotic apparatus of FIG. 3 respectively corresponding to the steps of FIGS. 4A, 4B and 4C.

In the present example, at the proximal end thereof the second portion 111 of each arm is formed with a locking seat 117, better observable in FIG. 5A and whose role will be clarified shortly.

As shown still in FIG. 3 and as illustrated above, the overall structure of the apparatus 100 is such that both arms 101 and 102 can be simultaneously inserted through the introducer body 103 and housed, during use, therein at the basic proximal portion 110 thereof.

Still in FIG. 3, transmission cables 108, intended to transmit motion to the most proximal joints (shoulder) of the arms 101 and 102 were represented purely by way of example; their role shall be explained hereinafter.

In the present embodiment, the apparatus 100 also comprises a locking element 114, or pin, which is adapted to be inserted longitudinally through the introducer body 103 centrally between the two arms 101 and 102 for locking the latter on the introducer body. The locking element 114 bears, at the longitudinal end thereof arranged distally during use, two transverse shaped projections, respectively indicated with 115 and 116, arranged on diametrically opposite sides and each adapted to be inserted in a respective locking seat 117 of a respective arm 101, 102.

Preferably, the locking element 114 has a tubular structure, i.e. a longitudinal interior lumen, indicated with 118 in FIG. 5A.

The methods for locking the robotic arms 101 and 102 on the introducer body 103 are described hereinafter.

Once the robotic arms are in the introduced configuration of FIG. 2I, the locking element 114 is introduced between the two arms, at an arrangement in which the projections 115, 116 are orthogonal to the transverse direction of extension of the second proximal portions 111. As shown in the sequence of FIGS. 4A-4C and 5A-5B, the locking element 114, once entirely introduced through the body 103, is rotated so as to couple such projections 115, 116 within the respective seats 117, where they are fittingly restrained, snap restrained or restrained through other means analogous retention means. Thus, by making the locking element 114 integral with the introducer body 103, the most proximal part of each arm 101, 102 is firmly locked on the introducer body 103.

With the aim of obtaining the abovementioned insertion and rotation movement, the locking element 114 may be connected to an external rigid support, for example a motor which makes it slide and rotate by 90°.

It should be observed that the previously described locking means allow locking the arms firmly in position after introduction thereof, providing a considerable mechanical stability thereto. Actually, once positioned within the abdomen, the arms form a single body with the introducer body 103. Furthermore, the central locking element 114 contributes to stiffening the assembly.

Thus, the described arrangement allows obtaining a stable support for the operating arms though operating through a single lumen (for example the belly-button) or access port. Such mechanical stability during the operation is a compulsory condition for the accuracy thereof. Furthermore, due to said stability, the robotic arms can exert considerable amounts of forces and thus be capable of performing any manipulating task required for surgery purposes.

Still, by operating through arms actuable from outside, the apparatus of the invention may exert considerable forces and obtain a satisfactory dexterity.

Lastly, due to said stable support for the arm, the apparatus however obtains an effective bimanuality though it can operate through a single lumen or access port.

Figure 5B:
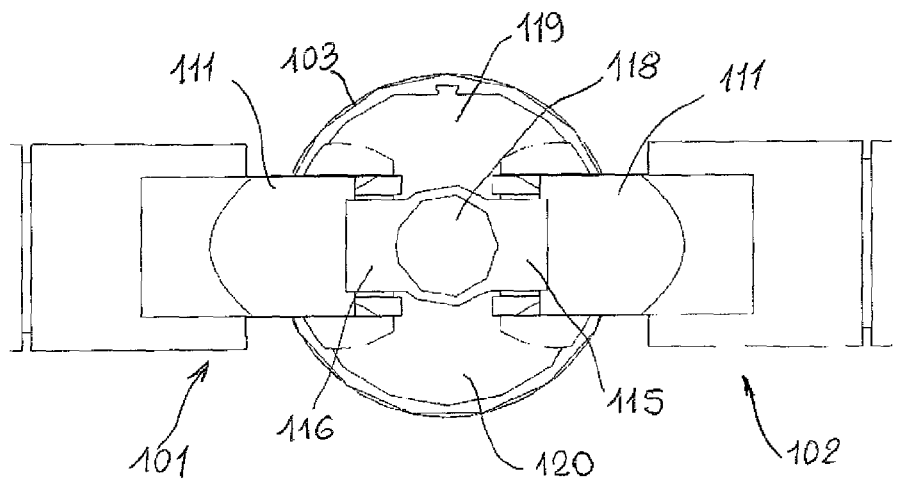

Furthermore, the locking element 114 being hollow, an inner lumen 118 for the introduction of operating or auxiliary elements is made available, even after the locking of the arms. FIGS. 5A and 5B also show how two lateral lumens 119 and 120 in the introducer body 103 remain available with locking completed.

Furthermore, the described arrangement guarantees a safe removal of the lock. Actually, given that the locking element 114 is made rigid and it can be maneuvered from outside, the risks related to the impossibility of folding the arms after completing the operation are minimum.

Figure 6:
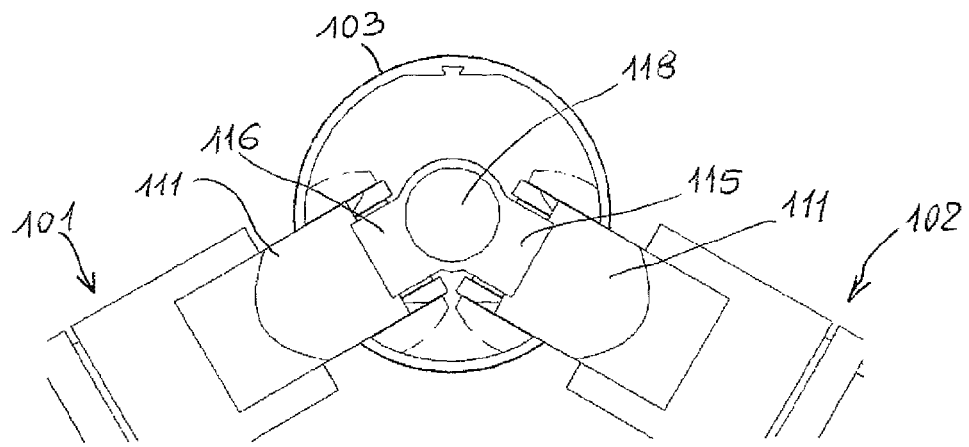
FIG. 6 shows a front view of a second variation of the means for locking the arms of the robotic apparatus of FIG. 1.

FIG. 6 shows a variation of the previously described locking means, in which the overall construction—and in particular the arrangement of the projections 115, 116 and of the relative seats 117—is not axial-symmetric. In such variation, the overall arrangement is such that, once locked on the introducer body 103, the second proximal portions 111 of the two arms 101 and 102 have incident longitudinal axes according to an acute angle α, which is also the relative angle according to which the two projections 115, 116 and obviously the respective seats 117 are arranged.

General Structure of a Robotic Serial Arm

Some preferred embodiments regarding the distal part of the serial structure arms 101 and 102, and in particular regarding the articulated joints thereof will be described below. Such description will be outlined with reference to a single arm, in particular to the first arm 101, but it can also be applied as it is to the second arm 102.

Figure 7:
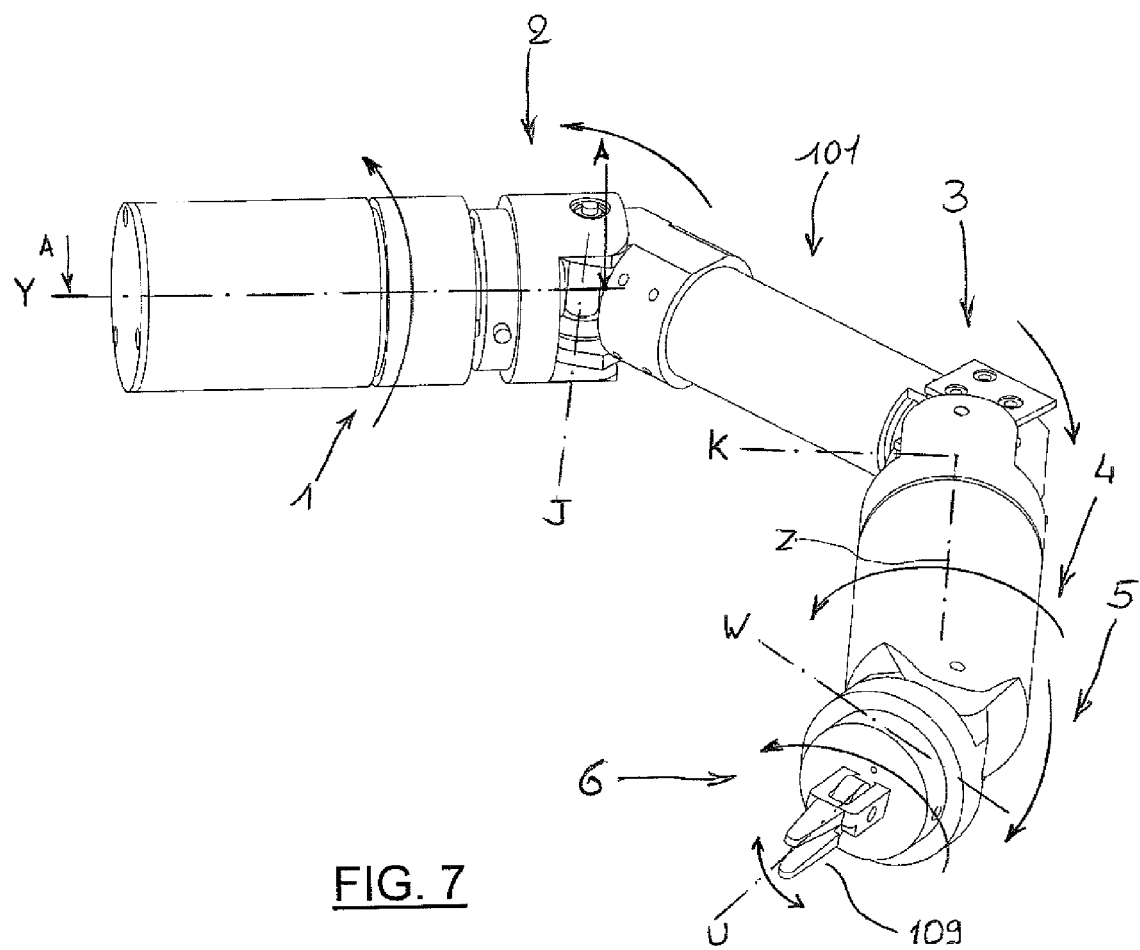
FIG. 7 shows a lateral perspective view of a first preferred embodiment of a robotic arm of the apparatus of FIG. 1.

With reference to FIG. 7, the serial structure arm 101, as previously mentioned, has six degrees of freedom, associated to an equivalent number of rotary joints and preferably distributed as follows:

a first torsional degree of freedom (rotation around longitudinal axis Y) associated to a first joint 1;
a second flexural degree of freedom (rotation around transverse axis J) associated to a second joint 2;
a third flexural degree of freedom (rotation around transverse axis K) associated to a third joint 3;
a fourth torsional degree of freedom (rotation around longitudinal axis Z) associated to a fourth joint 4;
a fifth flexural degree of freedom (rotation around transverse axis W) associated to a fifth joint 5; and
a sixth torsional degree of freedom (rotation around longitudinal axis U) associated to a sixth joint 6.

Therefore, the mobility and final dexterity of the arm 101 are obtained with an alternation of torsional and flexural joints arranged longitudinally in sequence along the arm.

A further opening/closing degree of freedom can be obtained at the level of the distal instrument 109, as schematically shown with an arrow in FIG. 7.

The first two joints 1, 2 will be defined "proximal" and the other four joints 3-6 will be defined "distal" for the sake of simplicity.

Following an anthropomorphic analogy, the first two joints 1 and 2 can be intended as associated to the degrees of freedom of a shoulder, the third joint 3 intended as associated to a degree of freedom for folding an elbow and the last three joints 4-6 intended as associated to the three degrees of freedom of a spherical wrist arranged at a "forearm".

First Variation for Transmitting Motion from External Actuators to the Proximal Joints of the Serial Robotic Arm and Variation of the System for Locking the Robotic Arms on the Introducer Body In the present embodiment and as described in detail hereinafter, the first two proximal joints 1-2 are actuated from outside through special transmission means, while the other four joints are actuated through local motor means.

Figure 8A:
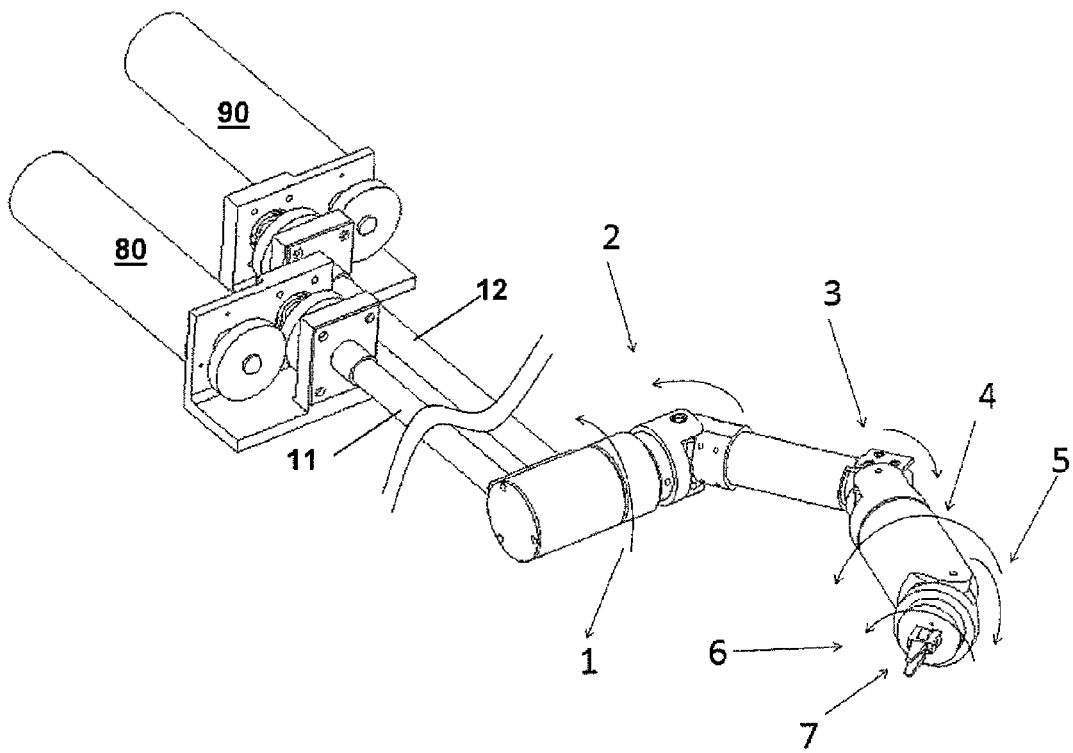
FIGS. 8A and 8B refer to the robotic arm of FIG. 7, respectively showing a perspective view and a longitudinal section thereof taken along line A-A of the latter figure and highlighting the provision of means for transmitting the motion from external actuators to the first two joints of the arm.
Figure 8B:
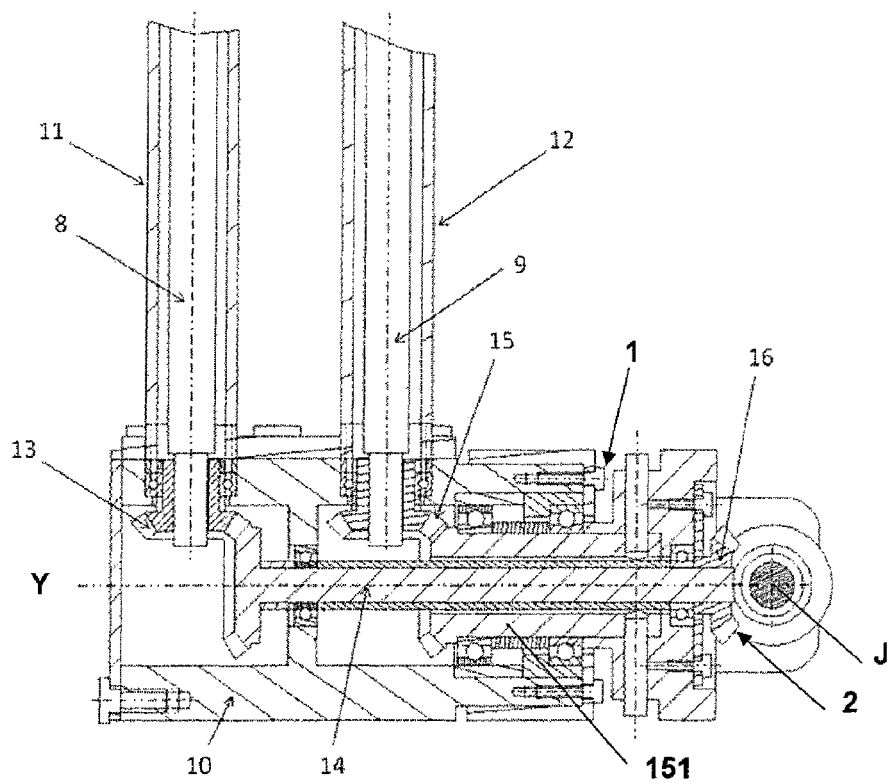

FIGS. 8A and 8B refer to a preferred embodiment of means for transmitting motion from external actuators 80 and 90 (schematically represented in FIG. 8A and per se known) to the proximal joints 1 and 2. In such embodiment, the transmission means are based on a bevel gear.

Getting deeper into detail, the two external actuators 80 and 90 are each connected to a respective first or second rotating drive shaft 8, 9 arranged at the beginning of the kinematic chain of the arm.

Each drive shaft 8, 9 is housed in a respective first or second sleeve 11, 12, in turn made integral with the introducer body 103 after insertion into the latter. Such fastening of the sleeves 11, 12 to the introducer body 103 can be obtained through known fastening means applied between the drive body 80, 90 and the introducer body 103.

Each drive shaft 8, 9 traverses an external casing portion of the arm 101, indicated with 10 and associated to the two joints 1 and 2, and it is removably coupled thereto through roller bearings or equivalent connection means.

The casing portion 10 is also integrally joined to the two sleeves 11 and 12. Thus, the base of the robotic arm 101, at an operating position, is rigidly and integrally anchored to the introducer body 103. Therefore, in this embodiment a locking different from that described with reference to FIGS. 3 and 4A-6 is provided for.

The transmission means described herein also comprise a first and a second bevel gear, respectively 13 and 15, each integrally joined to a respective drive shaft 8, 9.

The first bevel gear 13 transmits motion to a shaft 14 which is extended along the longitudinal axis Y and which, through a further distal bevel gear 16 coupled with a corresponding further component of the joint 2, provides the motion to the latter.

The second bevel gear 15 transmits motion to a hollow shaft 151 which provides the movement to the joint 1. In particular, the longitudinal shaft 14 which rotates within the hollow shaft 151 extends coaxially into the hollow shaft 151. Therefore, the movement of the second drive shaft 9 also causes the movement to the second joint 2. An independent movement of the first and second joint 1 and 2 through a suitable combination of the movements of the drive shafts 8 and 9, not described further hereinafter given that they are known to a man skilled in the art, can also be obtained.

In brief, the proposed transmission device (which could be subject to a separate and independent protection) is based on a pair of drive shafts 8, 9 each coupled through bevel gears 13, 15 or equivalent means to a further shaft 14, 151 substantially orthogonal thereto, the shafts of this second pair being substantially orthogonal to the respective drive shafts 8, 9 and also being coaxial with respect to each other.

It shall be observed that the previously described embodiment allows actuating the two proximal joints with a mechanism extremely small in size.

Figure 9:
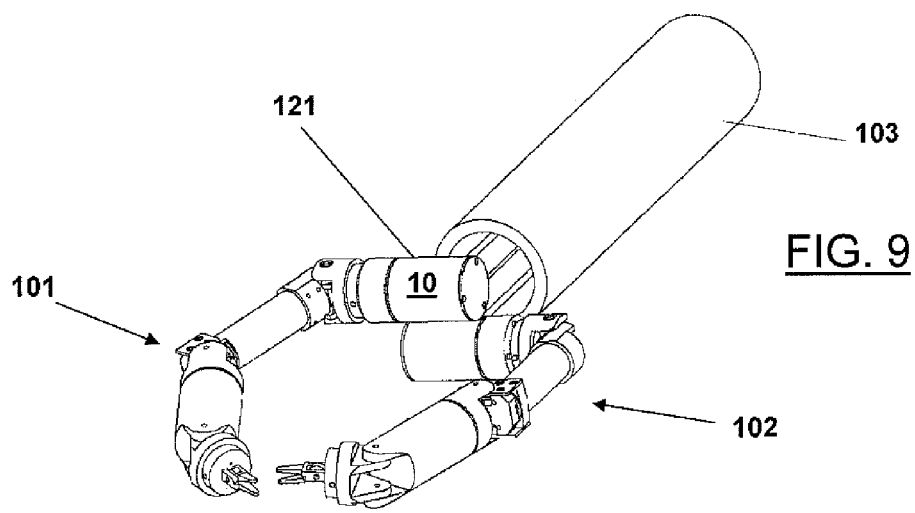
FIG. 9 shows a perspective view of the robotic apparatus of FIG. 1, showing a variant embodiment for the relative arrangement of the two arms.
Figures 10A, 10B:
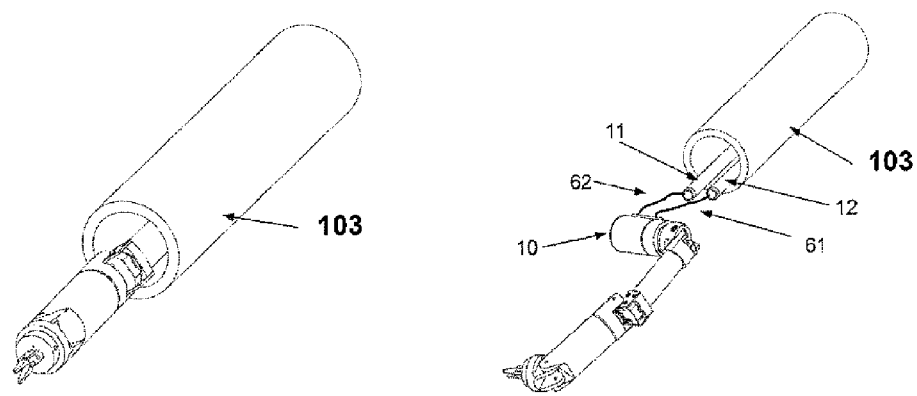
FIGS. 10A and 10B each show a perspective view of the robotic apparatus of FIG. 9 in a respective step for introducing an arm thereof into the introducer body.

As previously mentioned, the previously described structure requires a method for inserting and locking the robotic arms through the introducer body different from that of FIGS. 2A-2I and shown in FIGS. 9 and 10A, 10B.

FIG. 9 shows the apparatus 100, highlighting the relative arrangement of the two arms 101 and 102, particularly regarding the portions of the first two proximal joints 1 and 2 and according to the preferred embodiment thereof described last with reference to FIGS. 8A and 8B.

In order to obtain the configuration of FIG. 9 and also with reference to FIGS. 10A and 10B, the two arms 101 and 102 can be inserted into the introducer body 103 one at a time. During the insertion, each arm is supported by two cables 61 and 62, each connected to a respective sleeve 11, 12. Upon inserting the arms 101 and 102, the hollow shafts 11 and 12 are also introduced through the introducer body 103 and the two cables 61 and 62 connected to each arm are pulled from outside, together with the whole arm so as to introduce the sleeves 11 and 12 into the respective seats within the casing 10.

Thus also in this embodiment the robotic arms 101, 102 are formed with a first and a second proximal portion, the latter indicated with 121 in this case, which is arranged, during use, substantially orthogonal to the longitudinal axis X of the introducer body 103.

Figure 11:
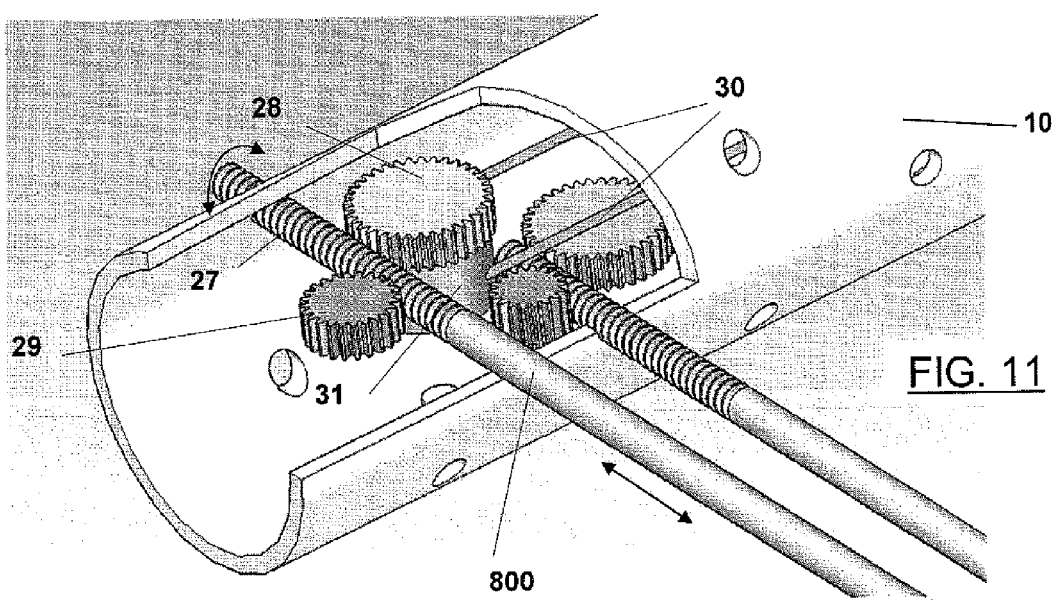
FIG. 11 shows a perspective view of a variation of the means for transmitting the motion from external actuators to the first two joints of the arm of FIG. 7.

Second Variation for Transmitting Motion from External Actuators to the Proximal Joints of the Serial Robotic Arm According to a variation of the arrangement shown in FIGS. 8A and 8B, the external actuation of the "shoulder" joints 1 and 2 provides for the use of respective translating shafts instead of rotating shafts, as shown in FIG. 11.

In particular, in the embodiment considered in this case, the transmission of motion to each of the joints 1 and 2 is obtained through a respective endless screw-toothed wheel mechanism. Thus, the transmission means comprise, for each joint, a translating drive shaft 800 which traverses the casing 10 of the arm 101 and has a helical thread 27 at the distal end thereof. Thread 27 is mechanically coupled with a toothed wheel 28 housed within the casing 10 and in turn adapted to transmit motion to the corresponding degree of freedom.

The transmission means considered in this case also comprise an idler wheel 29, arranged on the opposite side of the translating shaft 800 with respect to the toothed wheel 28. Such idler wheel 29 allows bearing the radial stresses on the drive shaft 800, due to the endless screw-toothed wheel coupling, which can be critical especially given the small dimensions of the mechanism.

The insertion of the drive shaft 800 through the casing 10 and between the wheels 28 and 29 can be carried out through an initial rotation thereof associated to an advancement equivalent to the propeller pitch of the thread 27. This allows introducing the shaft without actuating the corresponding degree of freedom. Subsequently, the translation movement of the shaft 800 will allow controlling the desired rotation of the joints 1 and 2.

Still in FIG. 11, the described transmission mechanism is represented coupled to an inner transmission of the motion obtained through cables 30, where a respective driving pulley 31 of each of them is integral with the respective toothed wheel 28.

Also the previously described translating shaft transmission means allow obtaining a configuration of the system like that shown in FIG. 9, through an insertion and locking system similar to that described regarding the rotating shaft actuation mechanism and shown in FIGS. 10A and 10B.

In brief, the proposed solution (which could be subject to a separate and independent protection) is based on the use of a translating shaft for each joint, coupled with the joint through a gear transmission mechanism or equivalent transmission mechanism and associated cable elements or equivalent elements.

It shall be observed that the previously described translating shaft solution allows reducing the diameter of the shafts, in this case subjected to traction/compression instead of torsion, and having more free space in the introduction channel of the body 103 as compared to the rotating shaft actuation of FIGS. 8A, 8B.

Third Variation for Transmitting Motion from External Actuators to the First Three Proximal Joints of the Serial Robotic Arm The following is a description of another embodiment of the means for transmitting motion from external actuators to the first three proximal joints 1, 2 and 3 of the arm 101, 102 based on a cable transmission mechanism.

Figure 12:
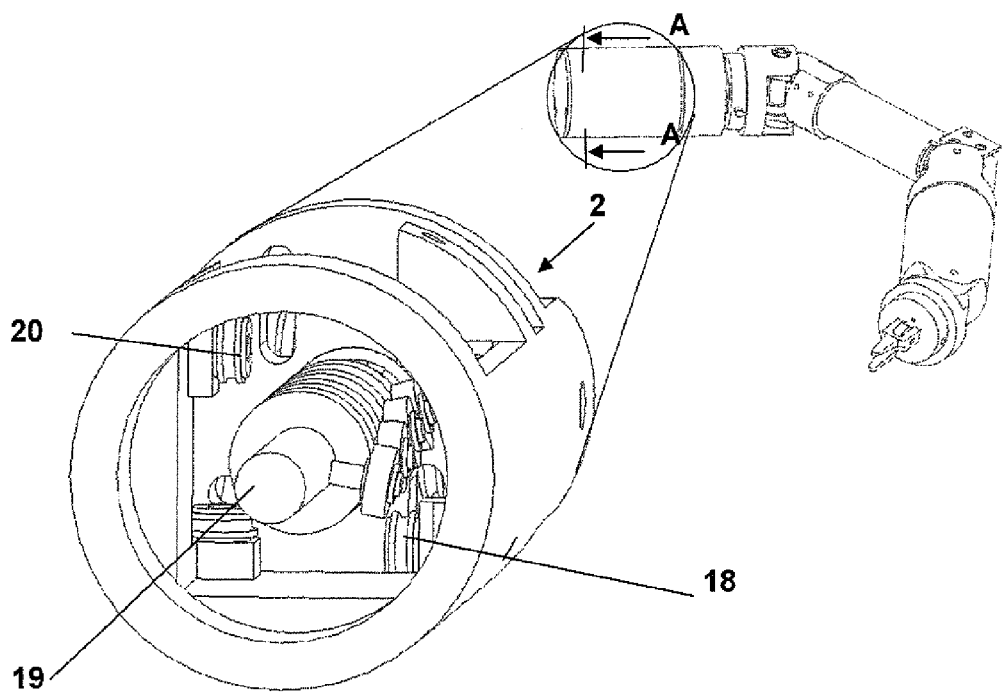
FIG. 12 shows a perspective view of a transverse section of the robotic arm of FIG. 7, showing a further variation of the means for transmitting the motion from external actuators to the first three joints of said arm.
Figure 13:
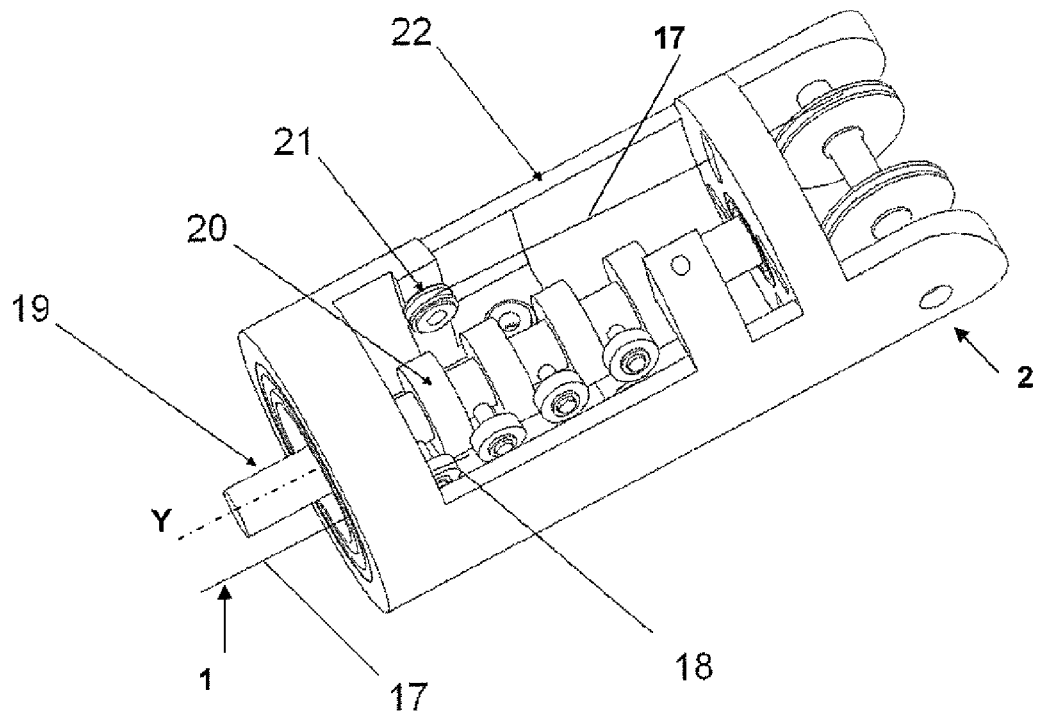
FIG. 13 shows a lateral perspective view, partly broken, of the arm of FIG. 12 showing an internal cable transmission mechanism.

With reference to FIGS. 12 and 13, the abovementioned cable transmission means provide for a particular arrangement of idler pulleys within the casing of the arm with the aim of allowing the cables for actuating the joints 2 and 3 to pass beyond the first torsional joint 1. In particular, such idler pulleys are positioned radially at a different distance from the axis of the torsional joint 1.

In the present embodiment, the joints 2 and 3 are actuated through a total of four cables, two for each one of them i.e. for each degree of freedom. As mentioned above, the four cables should pass through the first joint 1 and two of them also through the second joint 2.

Following the path of one the four cables that actuate the joints 2 and 3, a first cable 17 is passed through a first idler pulley 18—or first return pulley—positioned on a fixed shaft 19 (i.e. not rotatable with the joint 1) coaxial with the casing of the arm—such main casing/body of the arm is indicated in such case with 22—and thus with the axis Y of the arm. The first pulley 18 is arranged with the rotation axis thereof transverse and thus orthogonal to the axis Y of the fixed shaft 19.

Subsequently the cable 17 passes through a second idler pulley 20—or a second return pulley—positioned on the fixed shaft 19 coaxially with respect thereto.

From here, the path of the cable 17 proceeds towards a third idler pulley 21 or third return pulley—also arranged with transverse axis orthogonal to the fixed shaft 19 and integral with the external rotating casing 22 of the arm.

Then the cable reaches the joint 2. The passage of the cable beyond the joint 2 and for actuating the joint 3 is then accomplished through an idler mechanism similar to that described above and evidently housed in the arm portion interposed between the joints 2 and 3.

FIGS. 12 and 13 show further pulleys, besides the ones described, which are suitable for the passage of the other three cables through the joint according to the methods similar to those described above.

It is worth noting that the proposed transmission mechanism can also be associated to the above described embodiment with rotating shafts for actuating the first two joints and used for transmitting motion to the subsequent joints and also to the embodiment with translating shafts also for transmitting motion to the first joints.

It should be observed that the previously described mechanism achieves the following advantages:
- an efficient and reliable passage of the transmission cables through the proximal joints 1 and 2 and into an extremely small space;
- generally, the passage through a torsional joint in a compact arrangement, allowing an extensive rotation of the torsional joint with a transmission efficiency unaffected by the angular position of the torsional joint;
- the absence of torsion of the cables present in some solutions of the known art.

Still generally, the described mechanism allows actuating cables of several joints downstream of a joint arranged with the axis parallel to the initial longitudinal extension of the cables and in a small space, in that the axis of the idler pulleys is arranged radially relative to the abovementioned joint.

An idler system like the one described above, which in the most general definition thereof is based on a plurality of idler pulleys arranged in sequence and wherein each pulley has an axis orthogonal to that of the adjacent pulley, may actually also be applied even in sectors different from the one considered herein. In particular, the described arrangement can be applied in any actuator device—even different from the articulated arm portion considered in this case—equipped with a torsional degree of freedom and a flexural degree of freedom. In the most general description thereof, such actuator device comprises:
- a main body (equivalent to the considered arm portion) having a torsional degree of freedom according to a longitudinal rotation axis (the axis Y considered above);
- a joint (the joint 2 in the arrangement described above) arranged at an end of such main body;
- means for transmitting flexural motion to such joint through the main body, such transmission means comprising a plurality of idler pulleys adapted to be engaged by at least one transmission cable, the idler pulleys being arranged at a variable radial distance relative to said longitudinal axis.

Figure 14:
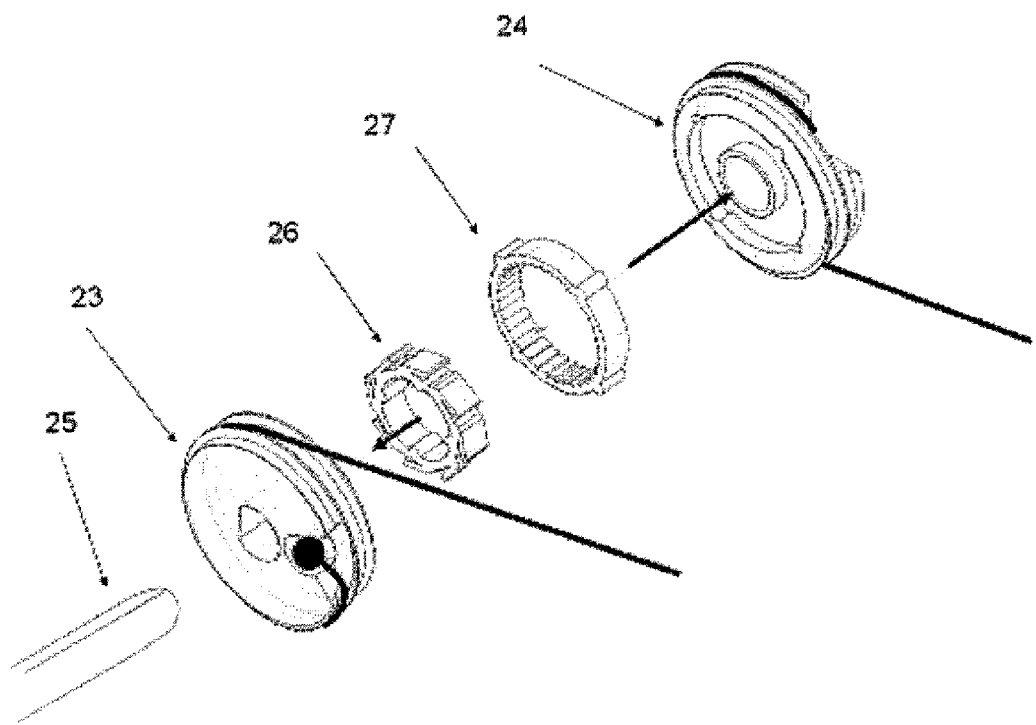
FIG. 14 shows an exploded view of a device for pre-stretching the arm of FIG. 12.

Now, with reference to FIG. 14, a device for pre-stretching the cables, which allows the latter to be always in a stretched condition before the actual operating step is also provided for in the present embodiment.

The abovementioned cable pre-stretching device is adapted to be housed in a small space such as within the proximal part of the arm (i.e. the abovementioned "shoulder").

For each transmission cable, the pre-stretching device provides for the use of two pulleys coupled to each other through a mechanism which allows a unidirectional rotation between the two pulleys.

In particular, a first stretching pulley 23 which is mechanically integral with a shaft 25 and a second stretching pulley 24 free to rotate on the shaft 25 is provided for each cable in FIG. 14. A first and a second grooved wheel 26 and 27, each arranged within a respective pulley 23, 24 and integral therewith are also provided for. The two grooved wheels 26 and 27 are shaped so as to form a mechanical coupling with the shaft 25 which counters a rotation in a direction of the respective pulley, while it leaves the rotation free in the other direction.

In particular, the first wheel 26 has an external saw-toothed profile, which is engaged with a corresponding internal step profile of the second wheel 27, allowing a stepping rotation in one direction (with the teeth sliding on the crests of the steps) and preventing rotation in the opposite direction due to the fact that the teeth abut against the shoulders of the steps. Thus, the cable can be pre-stretched by rotating the pulley in the free direction of rotation, until the desired preload is reached. The counter-rotation of the pulley is hindered by the coupling between the grooved wheels 26 and 27.

It should be noted that the provision of cable transmission means allows increasing the free space within the introducer body.

In a variation of the system, only the first two joints 1 and 2 are cable-actuated, while the joint 3 is actuated by a motor arranged inside, thus simplifying the overall mechanism.

Figure 15:
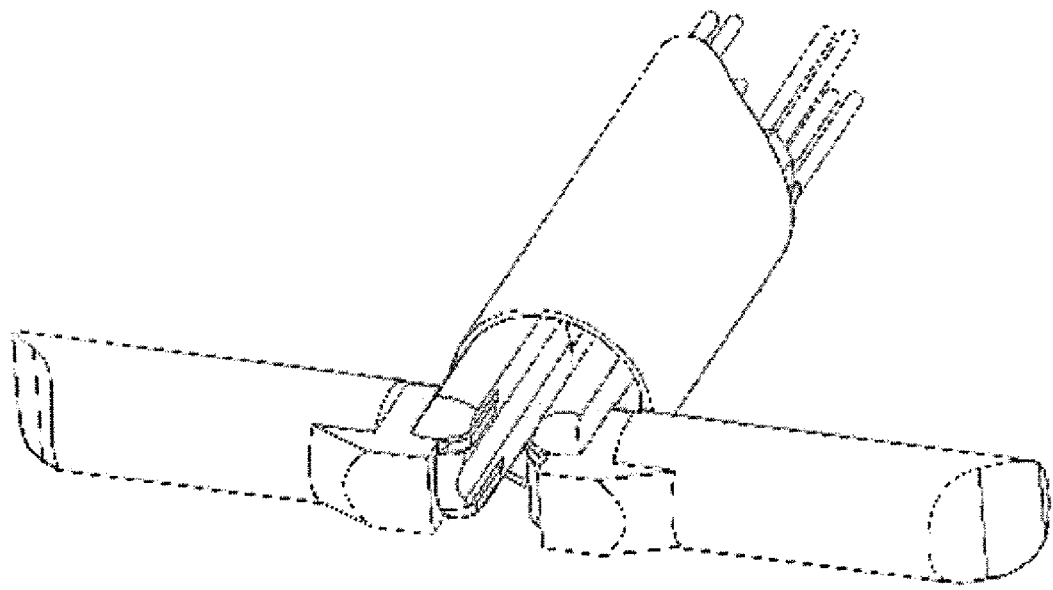
FIG. 15 shows a front perspective schematic view of the robotic apparatus of FIG. 1 incorporating the cable transmission means of FIG. 12.
Figure 16:
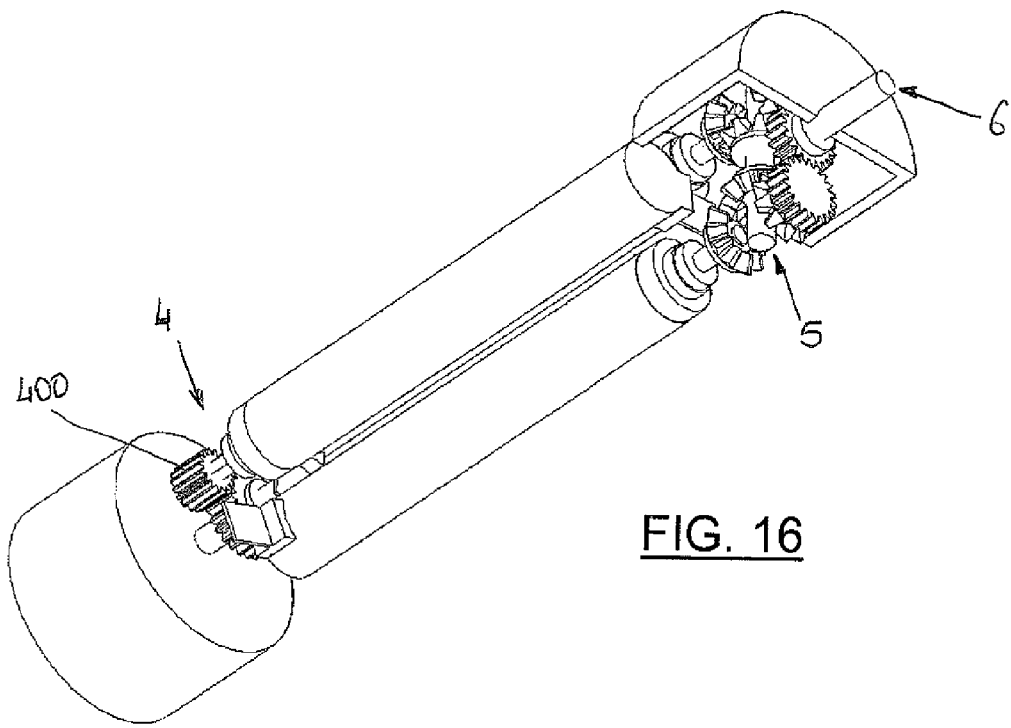
FIG. 16 shows a partly exploded lateral perspective view of a preferred embodiment of a distal part of the robotic arm of the apparatus of FIG. 1, compatible with the variations of the preceding figures.

The two or more arms partly actuated by cables can be arranged as shown in FIG. 15 according to the general architecture of the apparatus of FIG. 1 and with the first method for locking the arms described above.

Actuation of the Distal Joints of the Serial Robotic Arm

Now, with reference to FIGS. 16 and 17A-17C, as mentioned previously the distal joints 4-6 of each robotic arm 101, 102 of the apparatus 100 of FIG. 1 are moved through on-board drive means. Such on board actuation is accomplished through miniaturized motors, preferably electrical motors, brushless DC motors in the present example.

Regarding the joints 5 and 6, the proposed solution consists in a particular differential mechanism which allows reducing the overall space necessary for housing the two joints 5, 6 and allows housing the motors along the axis of the aforementioned "forearm". Such differential mechanism comprises a first and a second assembly of three gear wheels preferably of the conical type, each assembly being respectively indicated with 340 and 350, which are coupled to form the differential by using a train of three further gear wheels preferably straight-cut gear wheels arranged in transverse sequence and respectively indicated with 34 and 35 for the two lateral wheels and with 36 for the central wheel.

In particular, the first assembly of wheels of the conical type 340 comprises three wheels coupled to form a substantially C-shaped structure, and in particular a first and a second wheel 341 and 343 which have incident rotation axes. The wheel 341 has a rotation axis parallel to the longitudinal axis of the forearm, while the axis of the wheel 343 rotates around the axis W of a shaft 360, thus forming the degree of freedom 5 of FIG. 7. A third conical wheel 342 is interposed between the first two for coupling thereof and it is arranged with a rotation axis substantially orthogonal to that of the wheel 341. A symmetric arrangement is provided for the second assembly 350.

The intermediate conical wheels 342 and 352 of the two assemblies are idle on the intermediate shaft 360 of axis W.

The two lateral wheels 34 and 35 of the aforementioned train of wheels are respectively integral with the first conical wheel 343 of the first assembly 340 and with an analogous first conical wheel 353 of the second assembly 350.

The central wheel 36 is instead integral with the distal end, indicated with 37, of the robotic arm.

The conical wheel 341 of the first assembly 340 is instead integral with a drive axis of drive means 38 and a conical wheel 351 of the second assembly 350 is integral with other drive means 39.

Thus the end of the robotic arm has a so-called pitch (rotation around axis W) and roll (rotation around axis U) degree of rotation depending on whether the drive means 38 and 39 rotate in the same direction of rotation (pitch) or in the opposite direction (roll). Thus, the desired roll and pitch combination can be obtained through a suitable combination of the drive means 38 and 39.

Regarding the actuation of the of the torsional joint 4, further drive means 40 still arranged within the forearm with axis parallel thereto and associated to transmission means 400 preferably with straight-cut gear wheels meshing are provided for.

In the example considered herein, the joints 4, 5 and 6 thus have incident axes. Preferably, in the assembly 340 the reduction ratio between the wheels 341 and 342 is greater than 1 and it is equal to the reduction ratio between the wheels 343 and 342. This allows a rotation around the axis w of the shaft 360 greater than 90° without the wheel 343 impacting against the wheel 341.

It should be observed that the solution proposed for the actuation of the distal joints 4-6 allows achieving a high degree of miniaturization, though allowing suitable power values.

Figure 27:
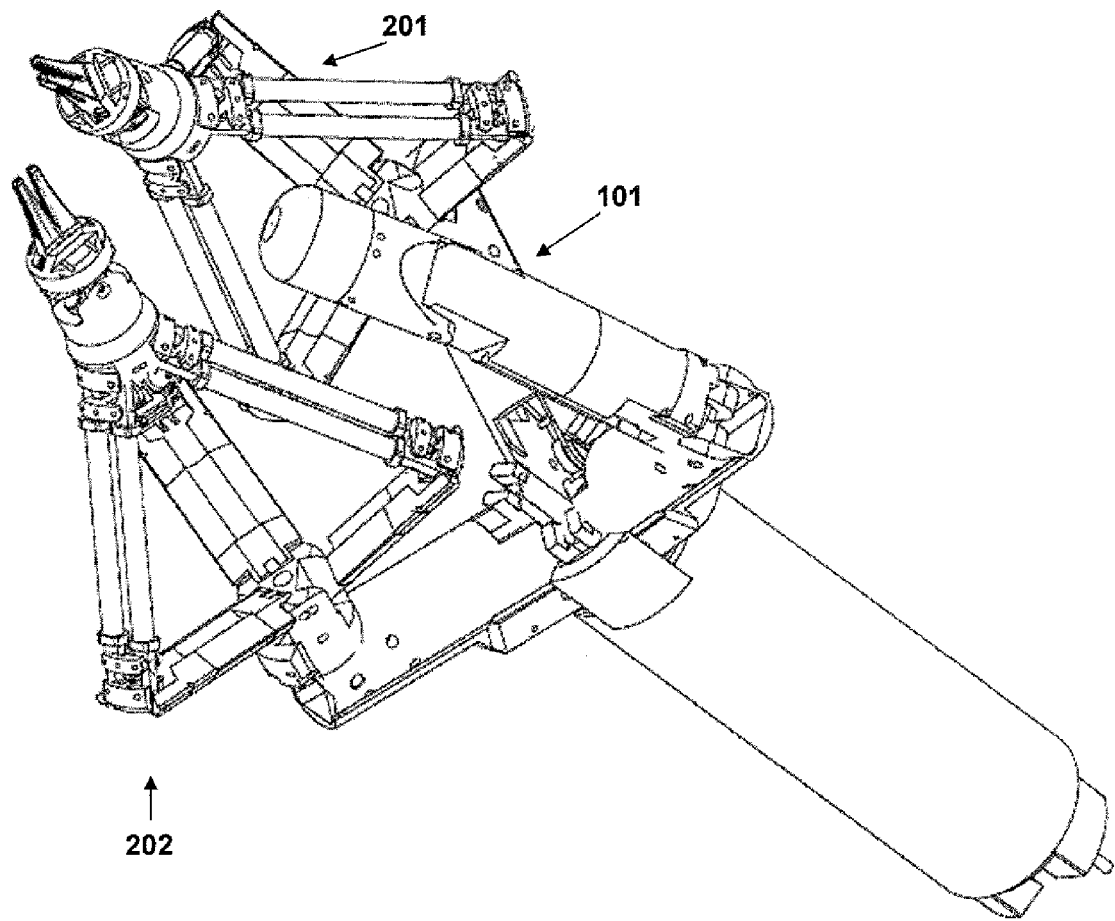
FIG. 27 shows a perspective schematic view of the robotic apparatus of FIG. 1 in another configuration incorporating two parallel/serial robotic arms analogous to that of FIGS. 19A, 19B and a serial arm analogous to that of FIG. 7.

It should also be observed that an actuation of serial joints like the one described beforehand can be provided for as a distal part of a generally hybrid arm 201, 202 like those shown in FIG. 27.

Lastly, it should be observed that that the differential mechanism described beforehand can also be subject of an independent protection, i.e. independent from the application to a robotic arm.

As previously mentioned, such differential mechanism is suitable for motion transmission in any system receiving or adapted to receive means for driving a flexural joint and a torsional joint arranged serially, given that it can be interposed between such drive means and said joints.

In such general definition, the transmission means comprise a first and a second assembly of three gear wheels, preferably of the conical type, and a train of three further gear wheels, preferably straight-cut gear wheels, which couple said first and second assembly to form a differential mechanism. Preferably, the gear wheels of each of the first and second assembly are arranged to form a substantially C-shaped structure, adjacent wheels having mutually orthogonal rotation axes, wherein two wheels have a rotation axis substantially parallel to the axis of the torsional joint and the third intermediate wheel has a rotation axis substantially parallel to or coinciding with the axis of the flexural joint.

Actuation of the Third Joint of the Serial Robotic Arm

Figure 18A:
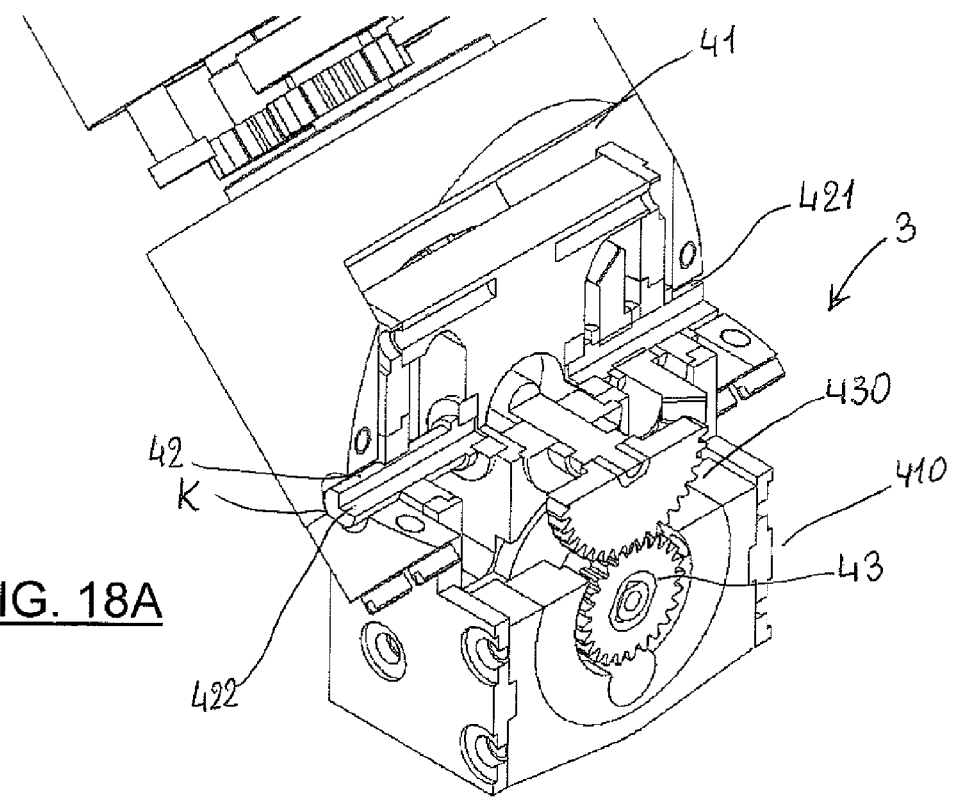
FIGS. 18A, 18B and 18C refer to a preferred embodiment of an intermediate joint of a robotic arm of the apparatus of FIG. 1, respectively showing a perspective view partly broken, a front sectional view and a lateral sectional view thereof.
Figure 17A:
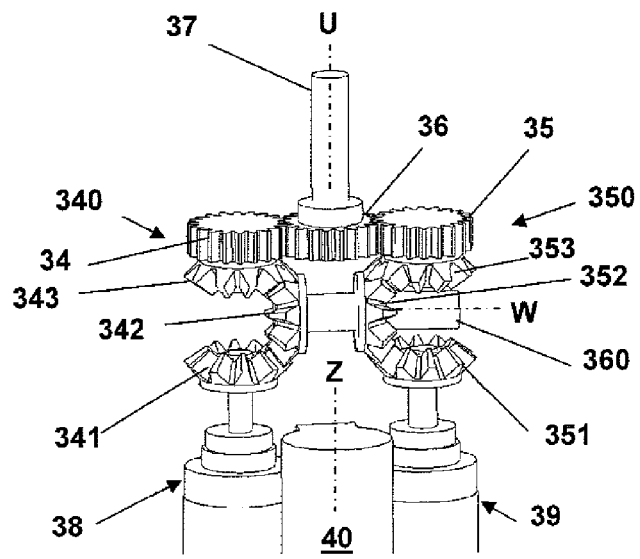
FIGS. 17A, 17B and 17C refer to a transmission mechanism of the arm portion of FIG. 16, respectively showing a perspective view, a plan view and a lateral view thereof.
Figure 17B:
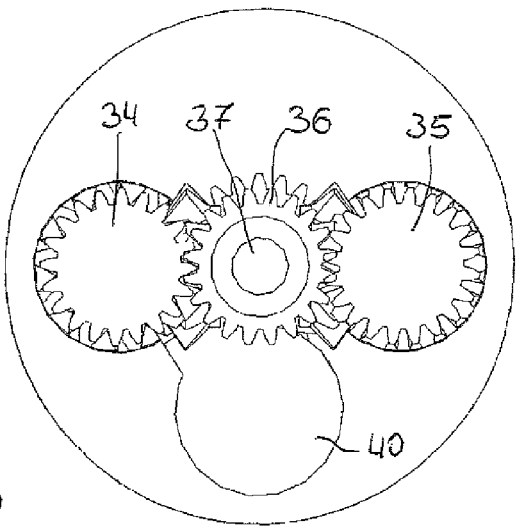
Figure 17C:
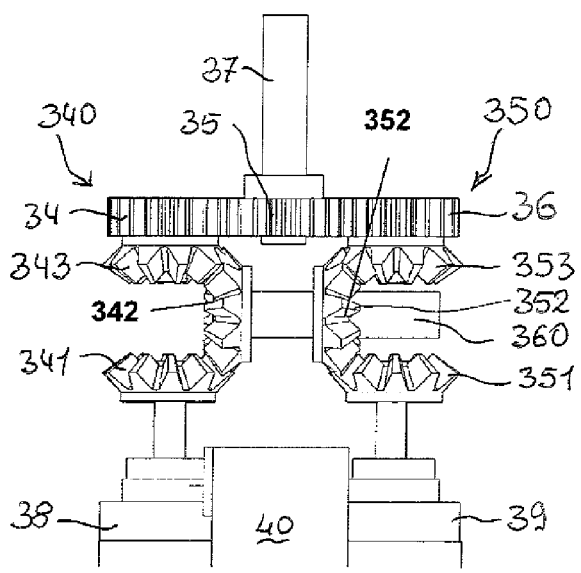
Figure 18B:
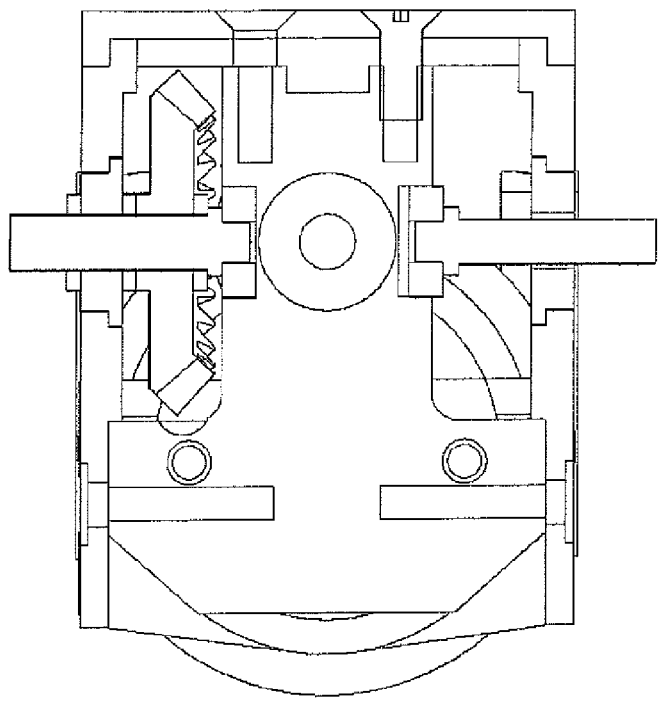
Figure 18C:
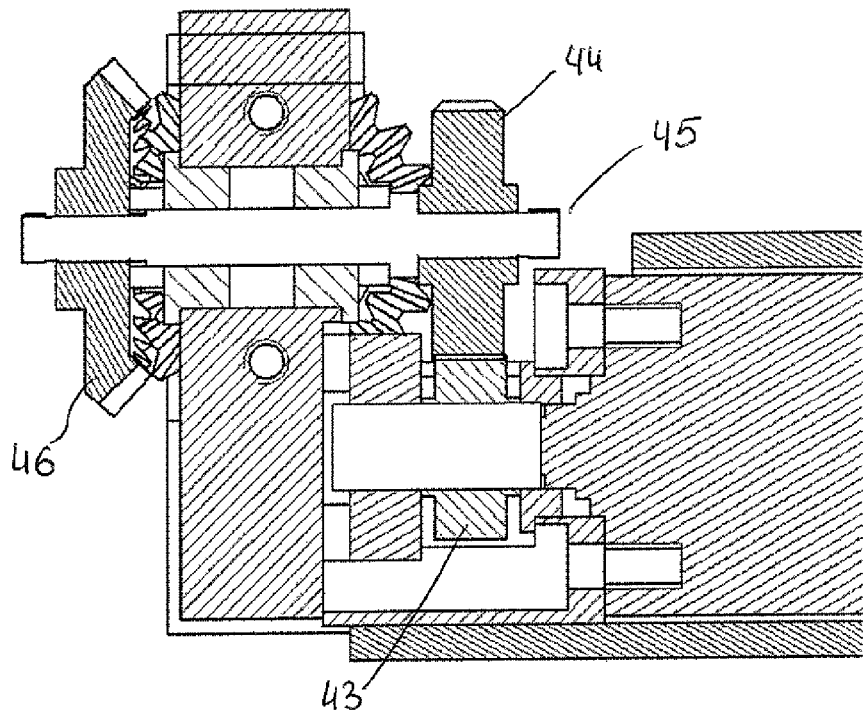

Now, with reference to FIGS. 18A-18C and according to a preferred embodiment, the joint 3 of the so-called "elbow"—which rotates a distal part 41 of the arm (i.e. the forearm) relative to a proximal part 410—provides for that the rotation shaft 42 extended according to the transverse axis K previously introduced be made as two distinct longitudinal portions 421 and 422. The motion is transmitted by a local drive wheel 43 to the axis K of the joint through a coupling of the conical wheels 430 at a right angle associated to the above-mentioned two parts 421 and 422 of the shaft 42.

It should be observed that the proposed solution for the joint 3 allows an extensive rotation, in particular an overall rotation exceeding 90 degrees and up to 130 degrees, with a compact gear transmission chain.

General Structure of a Hybrid Serial/Parallel Robotic Arm

Figure 19A:
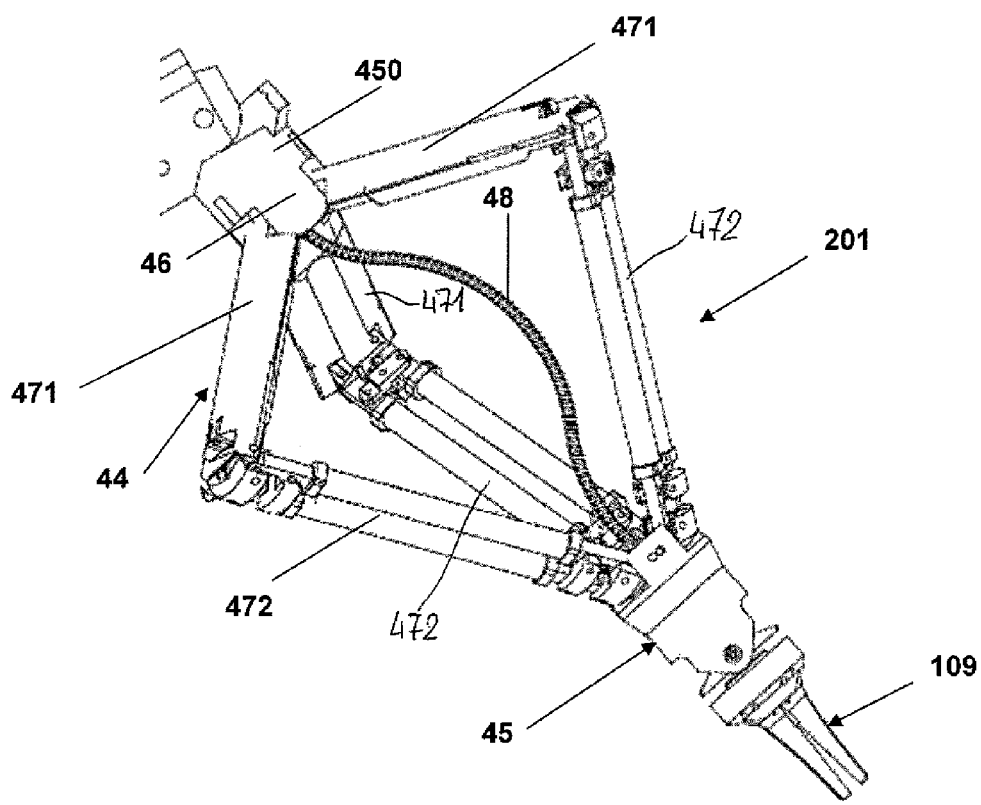
FIGS. 19A and 19B show respective perspective views—that of FIG. 19B as an enlargement of a detail—of a preferred embodiment of a robotic arm compatible with the apparatus of FIG. 1 and which provides for a hybrid parallel/serial arrangement of relative rotary joints.
Figure 19B:
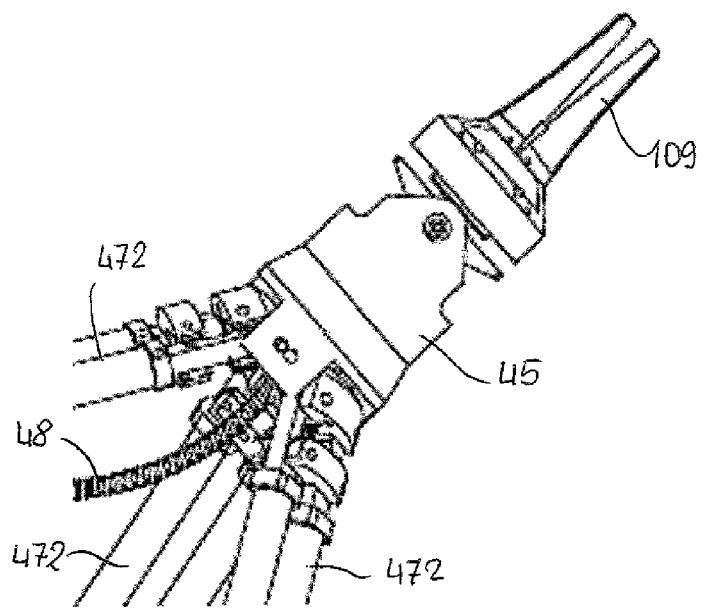

Now, with reference to FIGS. 19A and 19B, as mentioned previously the structure of the apparatus of FIG. 1 is also compatible with the provision of one or more of the arms thereof according to a hybrid parallel/serial arrangement of relative rotary joints.

In particular, in each of the parallel/serial arms 201, 202 the proximal joints 1-3 of the serial embodiment described above are replaced by a parallel structure 44 which allows a distal part 45 of the arm to have three translational degrees of freedom.

Getting deeper into details of the present embodiment, there are provided three articulation proximal points actuated by respective drive motors (for example brushless DC motors) positioned outside the apparatus 100, as illustrated further in detail shortly hereinafter. Such proximal articulation points comprise three respective hinges, one of which indicated by way of example with 46. The latter allow the rotation of an equivalent number of corresponding proximal segments 471 with respect to a base 450 of the parallel structure from which each of the proximal segments 471 depart.

As mentioned above, due to the movement combined with the three hinges 46 at the base 450, the distal portion 45 translates along three axis orthogonal to each other.

Each of the proximal segments 471 is then in turn articulated, at a distal end thereof, to a respective distal segment 472, the latter being articulated, at the other end, to the aforementioned distal portion 45.

The distal portion 45 also has other three rotational degrees of freedom positioned orthogonally with respect to each other, besides the translational ones mentioned above.

The actuation of the aforementioned three rotational degrees of freedom (and possibly the actuation of an additional degree of freedom at the tool 109) may either be performed using motors arranged on the distal segments directly or with an equivalent number of motors arranged outside. In the case of motors arranged outside, the power is transmitted to the segments through a cable actuation, the cables sliding along the axes of the parallel structure.

The actuation of the tool 109 can be transmitted along the arm through a cable and a sheath 48, represented by way of example in the figures considered in this case.

The combination of the six degrees of freedom allows the tool 109 positioned at the tip to reach the areas the surgeon is operating on, both in terms of position and angle.

FIG. 20 shows—in further detail—the actuation of the articulation points 46 of the present embodiment, in an operative configuration of the robotic arm. As previously mentioned, such actuation occurs through motors outside the body of the patient and an associated cable transmission. In particular, the external motors actuate drive pulleys 49 through respective axes, the pulleys—by means of cables 50—controlling the degrees of freedom. Such cables 50 are routed into the introducer body 103. A series of idler and return pulleys 51 guide the cables 50 towards the opening and coupling mechanisms of the arm and towards the respective joints to be actuated within the robotic arm.

Also in this embodiment the robotic arm 201 provides for a first and a second proximal portion, the latter indicated in this case with 131 and which is arranged, during use, substantially orthogonal to the longitudinal axis X of an introducer body 603 which will be described hereinafter.

Exemplifying Method for the Insertion of the Hybrid Robotic Arms Through the Introducer Body With reference to FIGS. 22A to 25, the following is a description of the preferred methods for introducing the hybrid robotic arms described above into the body of the patient.

In the embodiment considered in this case, an introducer body 603 modified with respect to the one described previously with reference to the serial structure of the arms will be used. Such introducer body 603 is inserted into the abdominal cavity of the patient, exemplified with a curved line L in FIGS. 22A and 22B.

The introducer body 603 has an operating channel which allows the passage of the surgical arms and the auxiliary instruments. Guides for facilitating the insertion of the surgical arms can be formed on the walls of such operating channel.

Figure 22C:
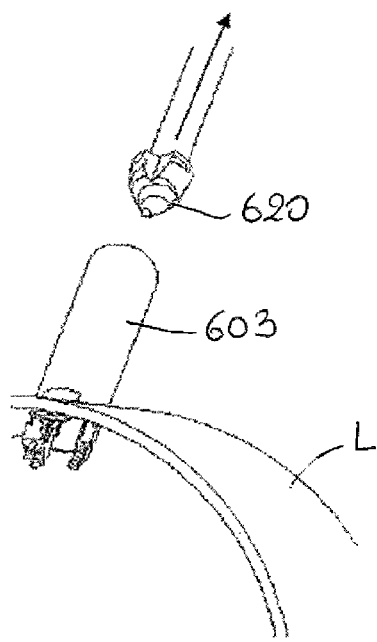

In the embodiment shown in FIGS. 22A-22C, a front incision means 620, whose function is to create an opening for the insertion of the introducer body 603 or facilitate insertion thereof in cases where the opening was already present can be associated, and in particular removably associated, to the introducer body 603 described above. Upon terminating the insertion of the introducer body 603, the incision means can open to allow the insertion of the arms or be removed directly, as shown in FIG. 22C.

Figure 22D:
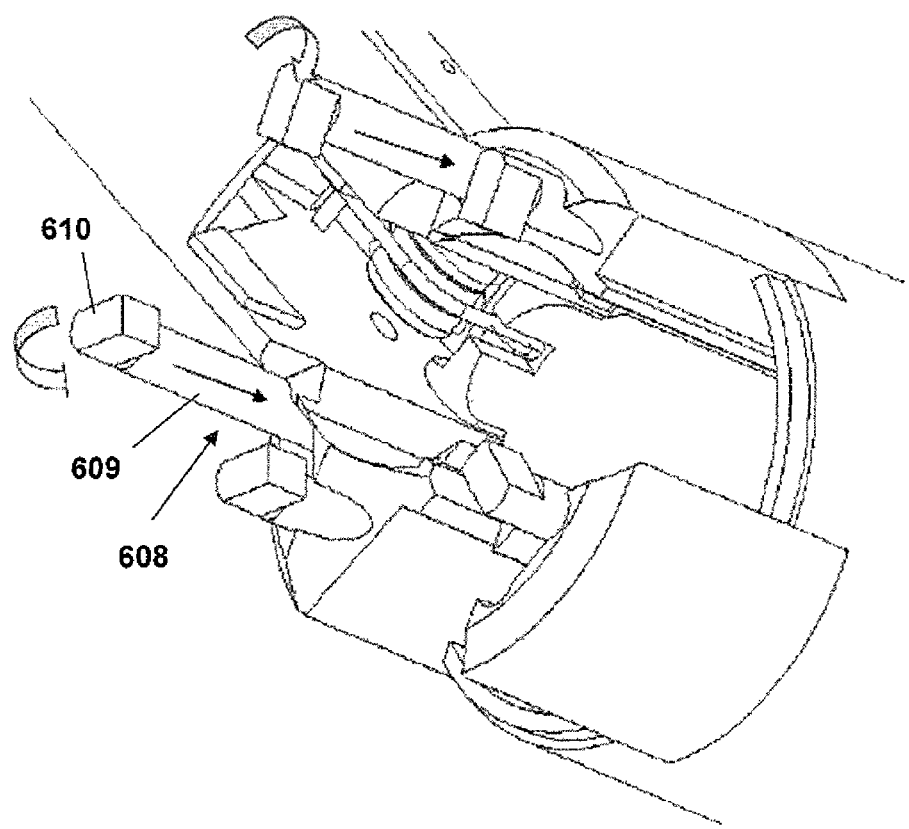
FIGS. 22D and 22E each show a perspective view of the same enlarged detail of the introducer body of FIG. 22A.

The introducer body also has locking means, intended for reference and rigid positioning of the arms, which are indicated in their entirety with 608 and better shown in FIG. 22D. As shown in this figure, locking means 608 comprise a plurality of elongated elements, typically in form of a rod indicated with 609, housed at the inner walls of the introducer body 603 and extended longitudinally parallel to the latter and thus to the longitudinal axis X of the introducer body. Each rod 609 bears, at a distal end thereof, a lateral hooking element or projection 610, so as to form a substantially L-shaped configuration of the rod. In the present embodiment, there are provided six rods 609, approached two by two for locking the same robotic arm, and distributed on the circumference of the introducer body 603.

The rods 609 slide along and rotate around a longitudinal axis thereof substantially parallel to the longitudinal axis X of the introducer body, so that the hooking elements 610 can be translated and rotated outwards with respect to the introducer body 603 and not hinder the insertion of the arms through them.

Figure 22E:
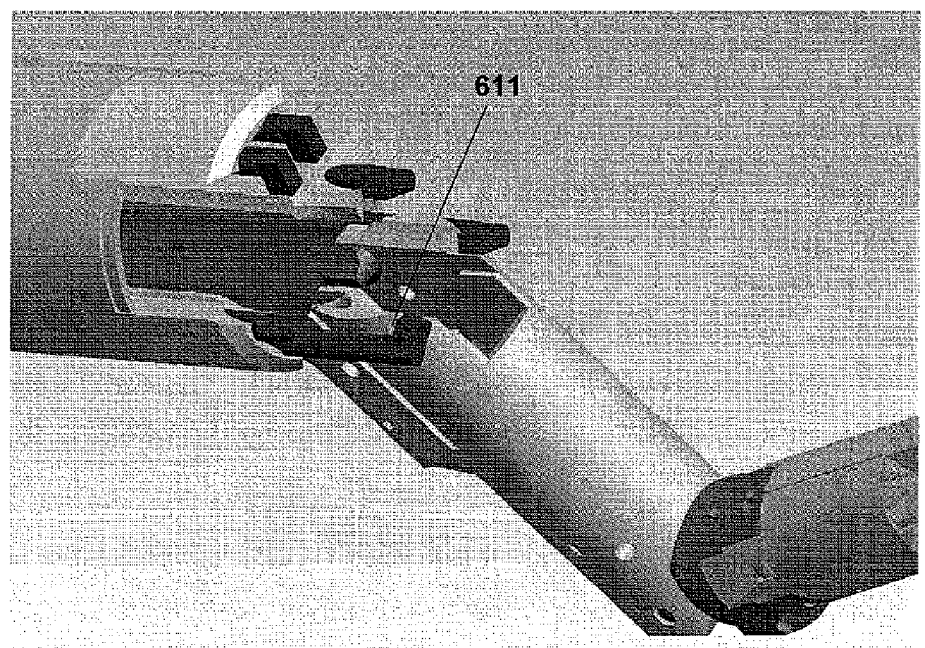

With reference to FIG. 22E, after inserting the arm, the element 610 for hooking the corresponding pair can be rotated once again and receded so as to engage them in special seats 611 formed on the proximal portion 131 of the arm, firmly restraining it to the introducer body 603. The rods 609 are thus locked on the introducer body 603 after hooking the corresponding arm, so as to complete the retention of said arm on the introducer body 603.

The introducer body 603 can then be constrained to an external structure capable of orienting and holding it at the desired position.

Figure 23A:
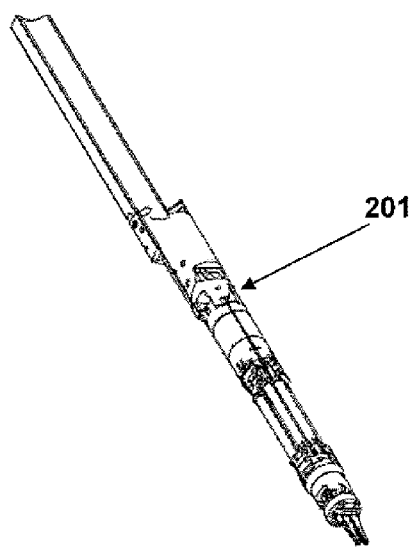
FIGS. 23A, 23B, 23C and 24 each show a perspective view of the robotic arm of FIGS. 19A, 19B and of the introducer body of FIGS. 22A-22E in a respective step for inserting the first into the second.
Figure 23A:
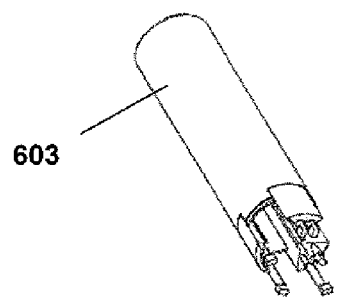
Figure 23B:
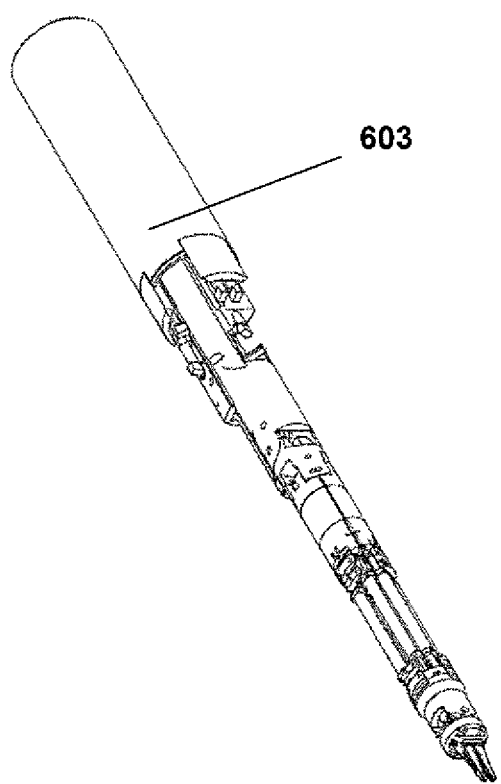

Getting further into the detail of the method for inserting the arms, once the introducer body 603 is positioned and the hooking elements 610 are rotated outwards with respect to the introducer body 603 as mentioned beforehand, an arm 201, 202 can be inserted one at a time, as shown in FIGS. 23A and 23B. During insertion, the arm 201 has a particular configuration for aligning the relative joints adapted to reduce the overall dimensions and hence facilitate insertion into the introducer body 603, shown in said figure. The guides possibly present on the walls of the introducer body facilitate such insertion.

Figure 23C:
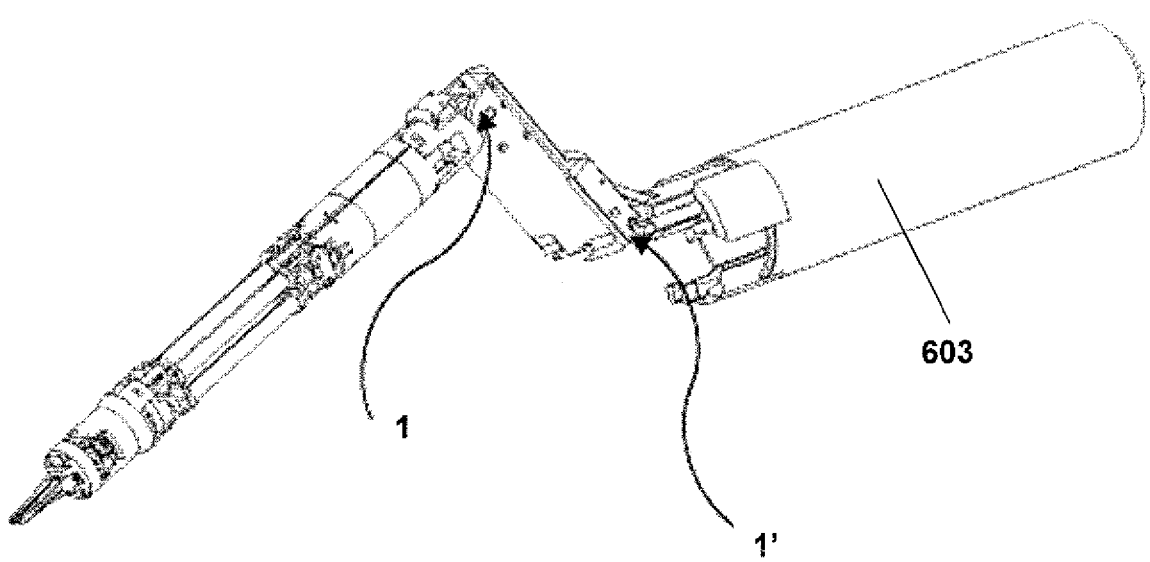
Figure 24:
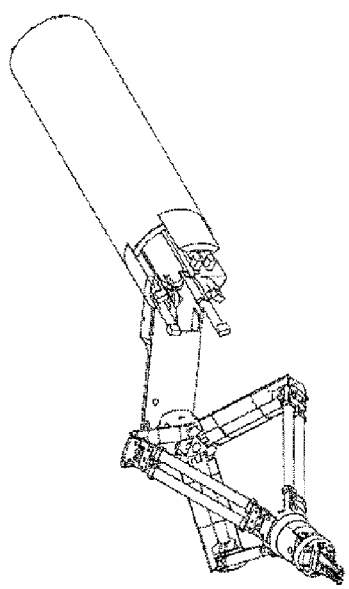

As shown in FIGS. 23C and 24, upon reaching the correct position the arm is opened and rotated at the proximal portion 131 (and in particular at the joint 1 and a proximal joint 1' thereof) so as to be hooked to the introducer 603 through the elements 610. Once the robotic arm has been positioned, the lumen of the introducer body is once again free for the insertion of other arms which follow the same procedure, as shown in FIG. 25.

It shall be understood that the substantial difference between the device 103 of FIG. 1 and the device 603 considered in this case lies in the fact that the introducer 103 has a common hooking system for all robotic arms. This implies that replacing a robotic arm requires removing all of them. However, it has an advantage lying in the fact that it is easy to construct and hence less expensive and more practical.

The introducer 603 may replace each arm without necessarily requiring removing the other arms (which can thus continue operating without being influenced by the replacement). This is due to the fact that each robotic arm has its own anchoring system, independent from the others.

Figure 25:
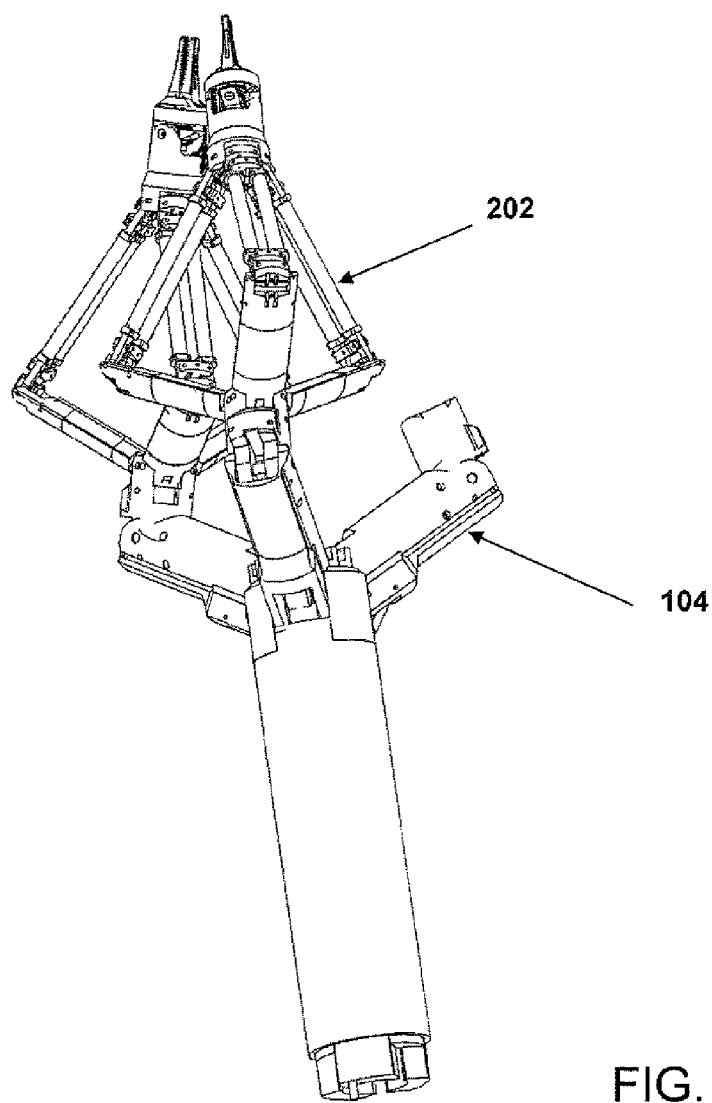
FIG. 25 shows a perspective view of two robotic arms obtained according to FIGS. 19A, 19B inserted into the introducer body of FIG. 22A.

As shown still in FIG. 25, a third arm comprising a vision system 104 is inserted besides the two arms in hybrid configuration.

The arm dedicated to the vision system not only reveals lesser problems in terms of forces to be transmitted and accuracy of the movements but it can also have a lower number of degrees of freedom with respect to the robotic arms expressly studied for performing surgery.

Upon terminating the procedure for inserting all the arms, a free operating channel is present within the introducer 603 for possibly allowing the use of complementary surgical instruments.

The configuration described above allows replacing the arms (for example to change the characteristics of the tool) regardless of the presence or absence of other components of the apparatus.

Figure 26A:
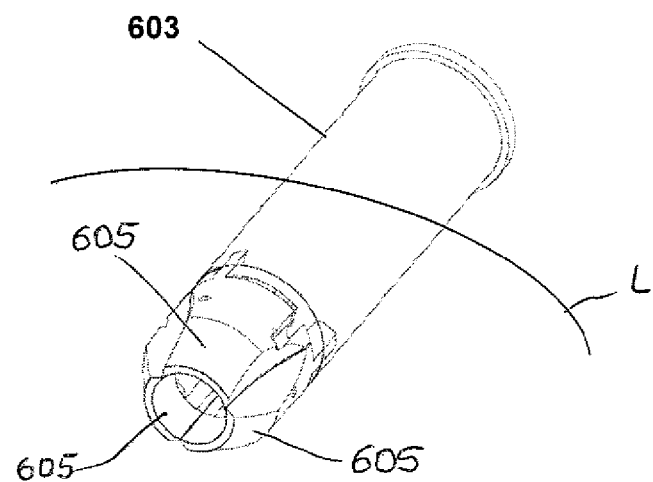
FIGS. 26A and 26B each show a perspective view of a variation of an introducer body, respectively in a minimum overall dimension configuration and in a deployed configuration.
Figure 26B:
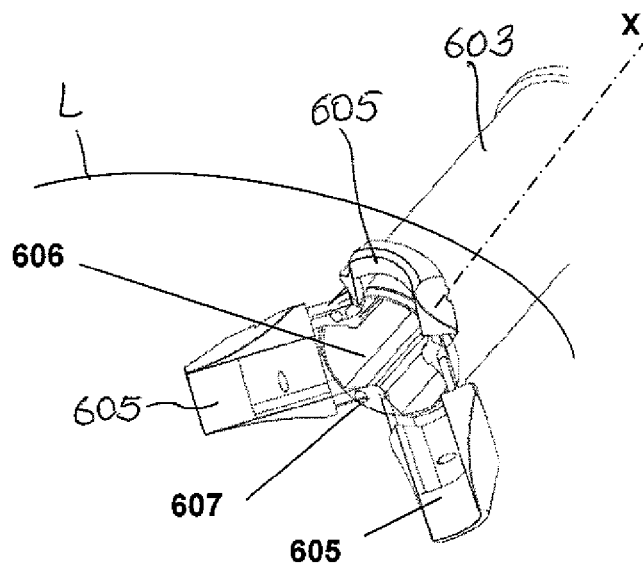

In the variation shown in the FIGS. 26A and 26B, the introducer body, still indicated with 603, further comprises, at the distal end thereof, a structure that can be deployed in a substantially flower-like manner, i.e. three projections 605 rotatably connected on the basic body along the circumference thereof and selectively actuable to pass the introducer body 603 from a minimum overall dimension configuration shown in FIG. 26A, wherein such projections are enclosed on the basic body, to a deployed configuration shown in FIG. 26B, wherein the projections are rotated outwards. This second configuration is adapted to allow the introduction of one or more hybrid arms into the abdominal cavity.

The hybrid parallel/serial solution for the structure of the robotic arm has the advantage of a greater rigidity of the system, a reduction of the mechanical clearances and the possibility of allowing providing cable actuation more easily. In particular, with respect to an entirely serial kinematic solution the hybrid solution allows providing an actuation system in which one or more motors are positioned outside the robot and the patient in an easier manner. This is due to the fact that taking the power from the motors to the distal degrees of freedom requires traversing a smaller number of joints of the kinematic chain of the robot.

Some Further Possible Embodiments

In the embodiments and variations described above, the robotic arms are actuated through mechanical transmission means such as for example cables, rotational or translational axes as described above. A particular technical solution can also provide for the use of pipes with pressurized fluids for the actuation of particular movements, such as for example opening and closing forceps or other instruments.

At this point, it should thus be observed that the robotic system of the invention, particularly in the previously described embodiments:

can be efficiently equipped with at least two arms, to perform bimanual surgery with a dexterity of the single arm comparable to the Da Vinci systems in terms of technical specifications;

it is capable of accomplishing performances similar to the Da Vinci system in terms of dexterity, operating speed and force on the end-effector, simultaneously reducing the invasiveness of the procedure due to the single access port approach;

it allows, with the presence of a lumen (0-30 mm) within the introducer body, the passage of additional instruments, such as a suture needle and thread, haemostatic sponge, sensors, etc, avoiding further incisions in the body of the patient;

it allows implementing, due to the on-board actuation of the arm of the distal degrees of freedom, a force feedback by reading the current absorbed by the motors (not present in the current robotic surgery platforms);

it allows, due to the mechanical solutions proposed for the anthropomorphic serial arm (for example stellar references for the cable actuation of the shoulder, the linear translational actuation for the proximal degrees of freedom, the mechanism for pre-stretching the cables in small spaces, the division of the elbow axis into two parts, the differential mechanism located in the wrist), that the overall dimensions can guarantee insertion thereof through one hole, simultaneously guaranteeing the desired specific performance;

thanks to the hybrid parallel/serial solution of the arm, a greater rigidity, it ensures a higher accuracy and fluidity of movement and a greater implementation simplicity for the cable-actuation;

thanks to the hooking mechanism it guarantees a rigid support for the arms, whereby the latter can be introduced sequentially exploiting the entire inner lumen (exploiting the entire inner diameter allows each arm to maximize the space available for the mechanisms and actuators);

the hooked mechanism also allows fixing more than two arms at a time, replacing only one or more if required (replacing the surgical instrument), and selecting the most advantageous space arrangements (in terms of work space and triangulation of the instruments) to complete the specific surgery;

according to the invention, the robotic arms find, by fixing to the introducer body and due to the presence of the locking element, an efficient support on which they can discharge the forces of their end effectors, thus achieving a high operating reliability.

Another important aspect lies in the fact that an actually bimanual behaviour of the system is accomplished in this case.

The apparatus of the invention is preferably applied in the abdominal district surgery. A possible specific application of the proposed system is represented by bariatric surgery for curing pathological obesity.

The present invention has been described with reference to preferred embodiments. However, other embodiments related to the same inventive concept can be provided without departing from the scope of the invention as defined by the appended claims.

The invention claimed is:

1. A surgical robotic apparatus comprising:
a surgical robotic arm comprising a torsional joint and a flexural joint forming serially arranged joints, said serially arranged joints providing respective degrees of freedom for said arm, said robotic arm being coupled to a drive mechanism configured to drive said serially arranged joints, said robotic arm further comprising transmission means placed between said drive means and said serially arranged joints,
wherein said transmission means comprise a first assembly and a second assembly of three gear wheels, and a train of three additional gear wheels coupling said first and said second-assembly to form a differential mechanism,
an introducer body for being inserted through a patient's skin to provide an access port to a surgical site, said introducer body comprising an internal longitudinal duct having a proximal inlet section and a distal outlet section, said internal longitudinal duct being suited for allowing the passage of said surgical robotic arm through said introducer body, and
locking means for integrally connecting a proximal part of said surgical robotic arm to said introducer body.

2. The apparatus according to claim 1, further comprising a front incision means inserted or movably insertable in said introducer body and suitable to help inserting said introducer body in the patient.

3. The apparatus according to claim 1, wherein said locking means comprise a locking element insertable in said longitudinal duct of said introducer body, said locking element capable of being integrally connected with said introducer body and a proximal part of said surgical robotic arm.

4. The apparatus-according to claim 3, wherein said locking element has an elongated shape.

5. The apparatus according to claim 3, wherein said locking element comprises at least one side projection and said articulated arm has a corresponding seat for housing said side projection.

6. The apparatus according to claim 5, wherein said side projection is a hooking tooth.

7. The apparatus according to claim 1, wherein insertion of said locking element in said introducer body defines two longitudinal side passages within said body on the outside of said locking element.

8. The apparatus according to claim 3, further comprising means for driving said locking element in a linear and/or rotary motion, arranged, in use on the outside of said introducer body.

9. The apparatus according to claim 1, wherein said locking means comprise a pair of locking longitudinal rods for said surgical robotic arm.

10. The apparatus according to claim 9, wherein said rods are arranged lengthwise parallel along a periphery of said introducer body.

* * * * *